United States Patent
Fukushima et al.

(10) Patent No.: US 10,305,052 B2
(45) Date of Patent: May 28, 2019

(54) TRIPTYCENE DERIVATIVE USEFUL AS MATERIAL FOR FORMING SELF-ASSEMBLED FILM, METHOD FOR MANUFACTURING SAID TRIPTYCENE DERIVATIVE, FILM USING SAME, METHOD FOR MANUFACTURING SAID FILM, AND ELECTRONIC DEVICE USING SAID METHOD

(71) Applicant: JAPAN SCIENCE AND TECHNOLOGY AGENCY, Kawaguchi-shi, Saitama (JP)

(72) Inventors: Takanori Fukushima, Yokohama (JP); Yoshiaki Shoji, Yokohama (JP); Fumitaka Ishiwari, Yokohama (JP); Tsuyoshi Sekitani, Tokyo (JP); Takao Someya, Tokyo (JP)

(73) Assignee: JAPAN SCIENCE AND TECHNOLOGY AGENCY, Kawaguchi-shi (JP)

( * ) Notice: Subject to any disclaimer, the term of this patent is extended or adjusted under 35 U.S.C. 154(b) by 167 days.

(21) Appl. No.: 15/325,943

(22) PCT Filed: Jul. 15, 2015

(86) PCT No.: PCT/JP2015/070220
§ 371 (c)(1),
(2) Date: May 23, 2017

(87) PCT Pub. No.: WO2016/010061
PCT Pub. Date: Jan. 21, 2016

(65) Prior Publication Data
US 2017/0279058 A1    Sep. 28, 2017

(30) Foreign Application Priority Data

Jul. 15, 2014  (JP) ................................ 2014-145269

(51) Int. Cl.
*H01L 51/00*  (2006.01)
*C07C 43/00*  (2006.01)
(Continued)

(52) U.S. Cl.
CPC ............ *H01L 51/052* (2013.01); *C07C 43/21* (2013.01); *C07C 43/215* (2013.01);
(Continued)

(58) Field of Classification Search
CPC .. H01B 1/00; H01B 1/12; H01B 1/121; C07C 43/21; C07C 69/712; H01L 51/00
See application file for complete search history.

(56) References Cited

U.S. PATENT DOCUMENTS 6,605,693 B1    8/2003  Becker et al.
9,825,232 B2 *  11/2017  Fukushima ............. C07C 43/21
(Continued)

FOREIGN PATENT DOCUMENTS

JP    2002-539286 A    11/2002
JP    2002-363154 A    12/2002
(Continued)

OTHER PUBLICATIONS

Norvez et al "Epitaxygens: Mesophase based on the Triptycene Molecular Subunit", J. Chem. Soc. Chem. Commun. 1990 1398-99. (Year: 1990).*
(Continued)

*Primary Examiner* — Mark Kopec
(74) *Attorney, Agent, or Firm* — Westerman, Hattori, Daniels & Adrian

(57) ABSTRACT

The present invention pertains to: a Janus-type triptycene derivative which is capable of forming a self-assembled film which does not depend on the material quality of a substrate; a self-assembled film using said Janus-type triptycene derivative; a structure having said film on a surface thereof;

(Continued)

a method for manufacturing said film; and an electronic device using said method.

24 Claims, 6 Drawing Sheets

(51) Int. Cl.
*H01B 1/00* (2006.01)
*H01L 51/05* (2006.01)
*H01B 1/12* (2006.01)
*C07C 43/21* (2006.01)
*H01L 29/786* (2006.01)
*C07C 43/215* (2006.01)
*C07C 43/225* (2006.01)

(52) U.S. Cl.
CPC .......... *C07C 43/225* (2013.01); *H01B 1/121* (2013.01); *H01L 29/786* (2013.01); *H01L 51/0529* (2013.01); *H01L 51/0545* (2013.01); *C07C 2603/90* (2017.05)

(56) References Cited

U.S. PATENT DOCUMENTS

| 2002/0150697 A1 | 10/2002 | Swager et al. |
| 2004/0106741 A1 | 6/2004 | Kriesel et al. |
| 2010/0143612 A1 | 6/2010 | Hirai |

FOREIGN PATENT DOCUMENTS

| JP | 2004-33824 A | 2/2004 |
| JP | 2004-506791 A | 3/2004 |
| JP | 2004-315461 A | 11/2004 |
| JP | 2004-359599 A | 12/2004 |
| JP | 2006-1968 A | 1/2006 |
| JP | 2006-512472 A | 4/2006 |
| JP | 2006-187225 A | 7/2006 |
| JP | 2007-277171 A | 10/2007 |
| JP | 2008-75047 A | 4/2008 |
| JP | 2008-308433 A | 12/2008 |
| JP | 2010-248467 A | 11/2010 |
| JP | 2012-111716 A | 6/2012 |
| WO | 03/055853 A1 | 7/2003 |
| WO | 2014/111980 A1 | 7/2014 |

OTHER PUBLICATIONS

Rybackova et al "Synthesis of highly symmetrical triptycene tetra- and hexacarboxylates", Synthesis 2007, No. 10, pp. 1554-1558. (Year: 2007).*

Norvex "Liquid Crystalline Triptycene Derivatives", J. Org. Chem. 1993, 58, 2414-2418. (Year: 1993).*

Sagiv, "Organized Monolayers by Adsorption. 1. Formation and Structure of Oleophobic Mixed Monolayers on Solid Surfaces", Journal of the American Chemical Society, Jan. 2, 1980, vol. 102, No. 1, pp. 92-98, cited in Specification (7 pages).

Nuzzo et al.,, "Adsorption of Bifunctional Organic Disulfides on Gold Surfaces", Journal of the American Chemical Society, 1983, vol. 105, No. 13, pp. 4481-4483, cited in Specification (3 pages).

Norvez, "Liquid Crystalline Triptycene Derivatives", J. Org. Chem., 1993, vol. 58, No. 9, pp. 2414-2418, cited in Specification (5 pages).

Seiki et al., "Rational synthesis of organic thin films with exceptional long-range structural integrity", Science, May 14, 2015, vol. 348, No. 6239, pp. 1122-1126, Fig. 1, cited in ISR (5 pages).

Norvez et al., "Epitaxygens-: Mesophases based on the Triptycene Molecular Subunitt", Journal of the Chemical Society, Chemical Corrununications, 1990, No. 20, pp. 1398-1399, compounds 1-8, cited in ISR (2 pages).

International Search Report dated Oct. 13, 2015, issued in counterpart International Application No. PCT/JP2015/070220 (1 page).

International Preliminary Report on Patentability (Form PCT/IB/373) issued in counterpart International Application No. PCT/JP2015/070220 dated Jan. 17, 2017, with Form PCT/ISA/237. (5 pages).

* cited by examiner

[FIG.1]
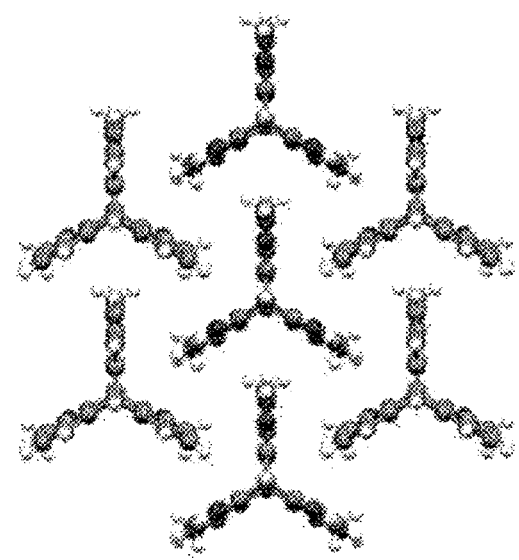
[FIG.2]
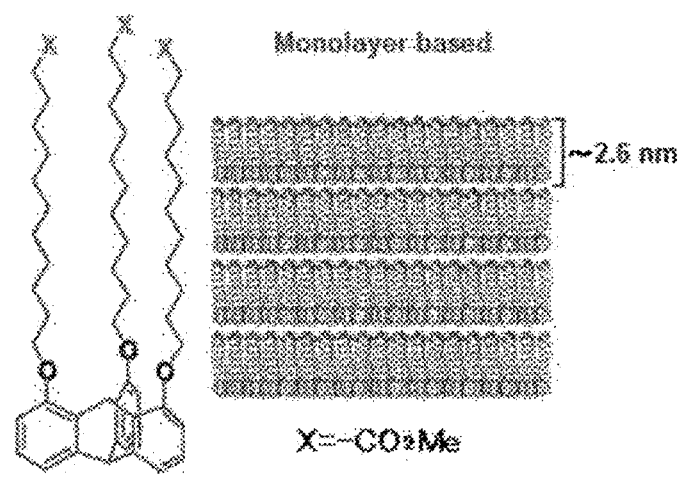

[FIG.3]
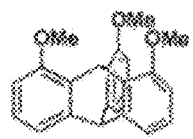
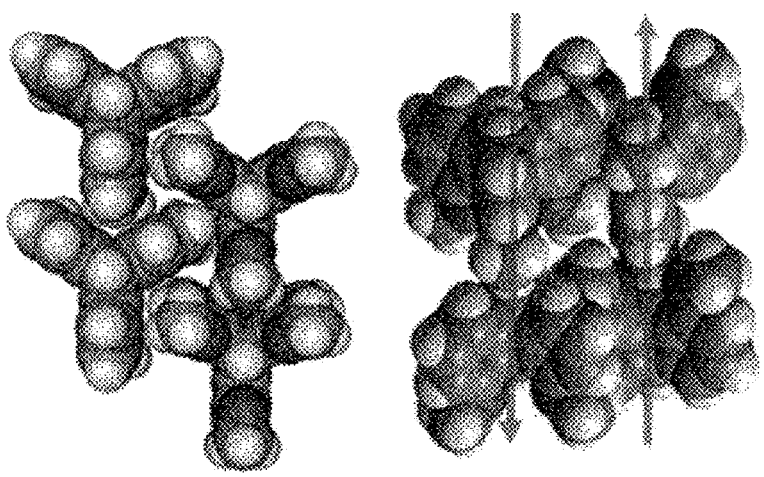
[FIG.4]
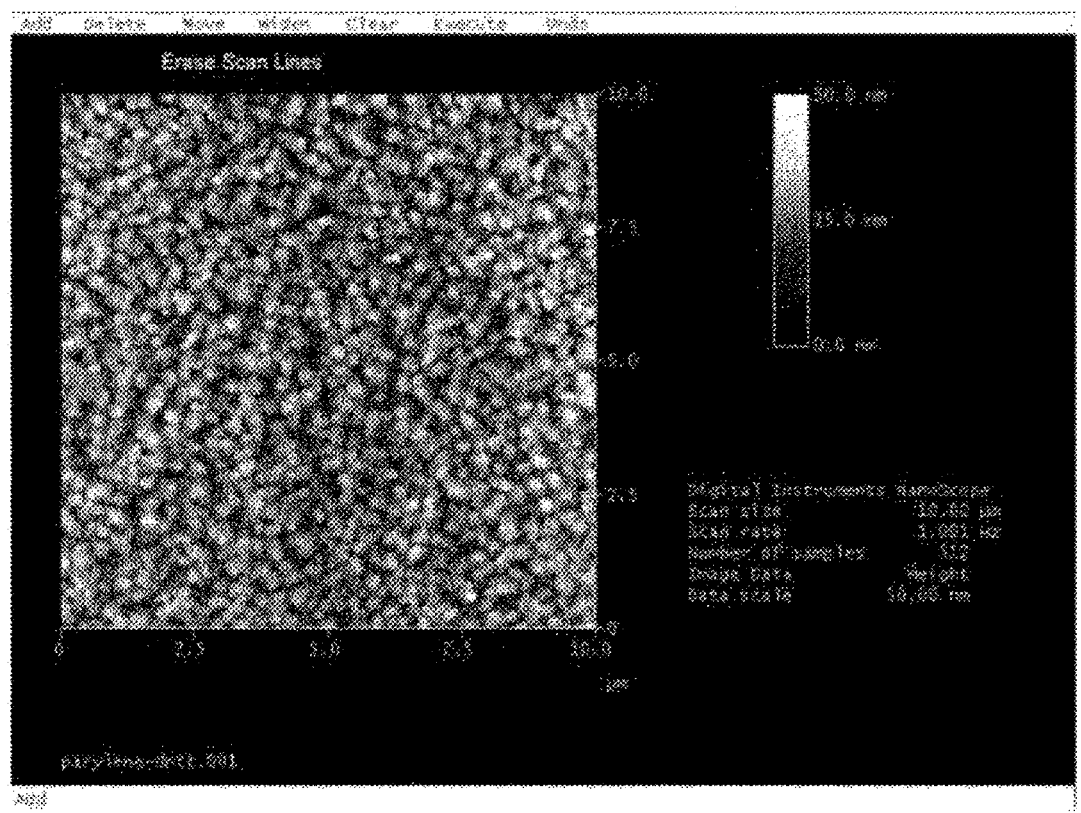

[FIG.5]
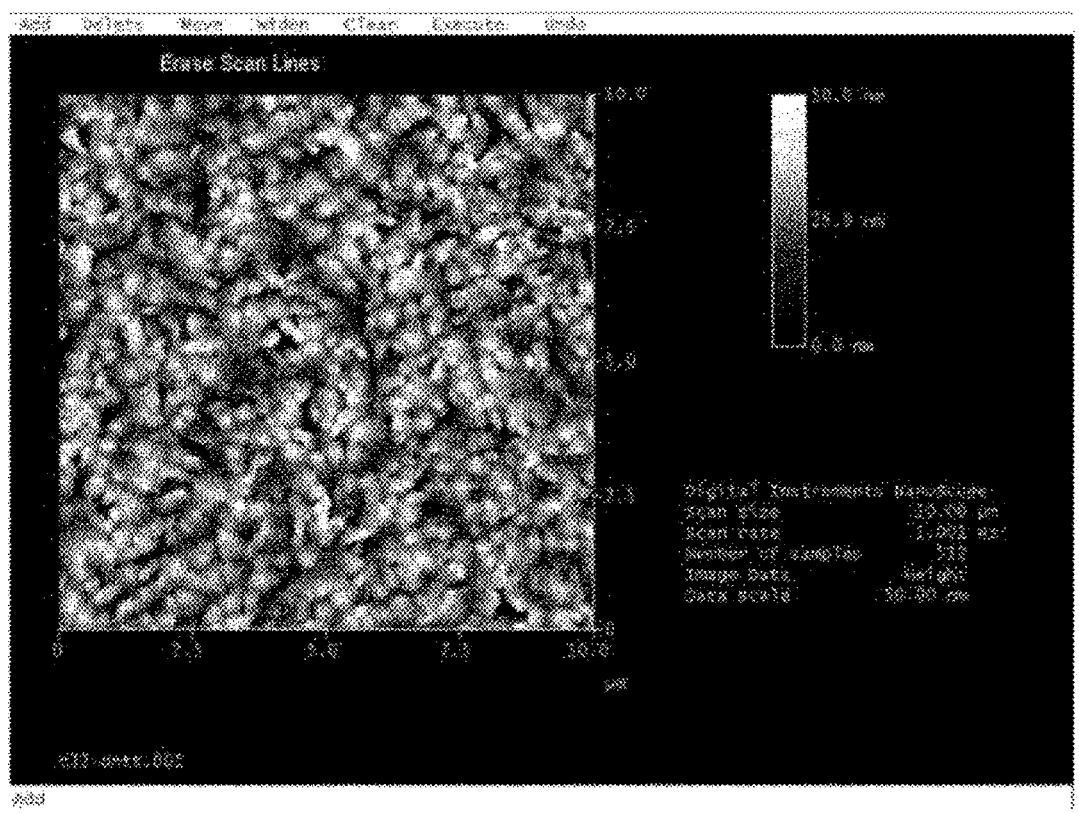

[FIG.6]
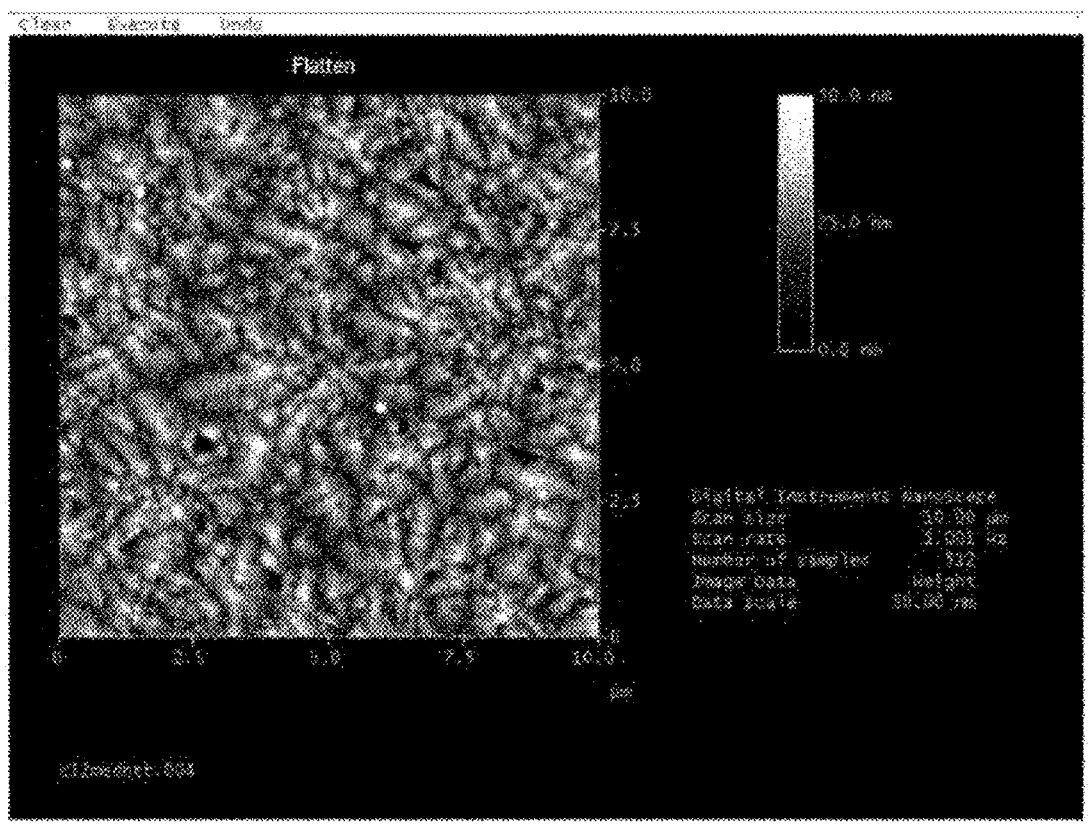
[FIG.7]
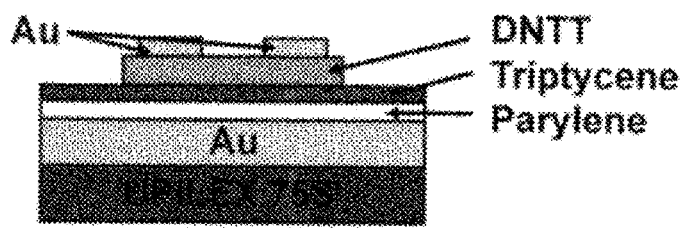

[FIG.8]
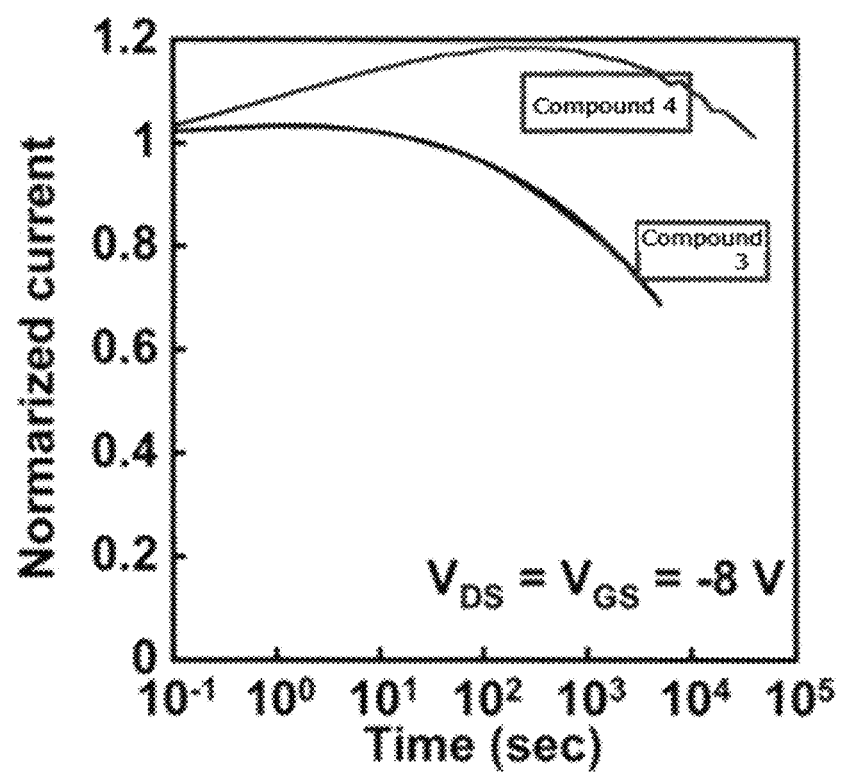

[FIG.9]
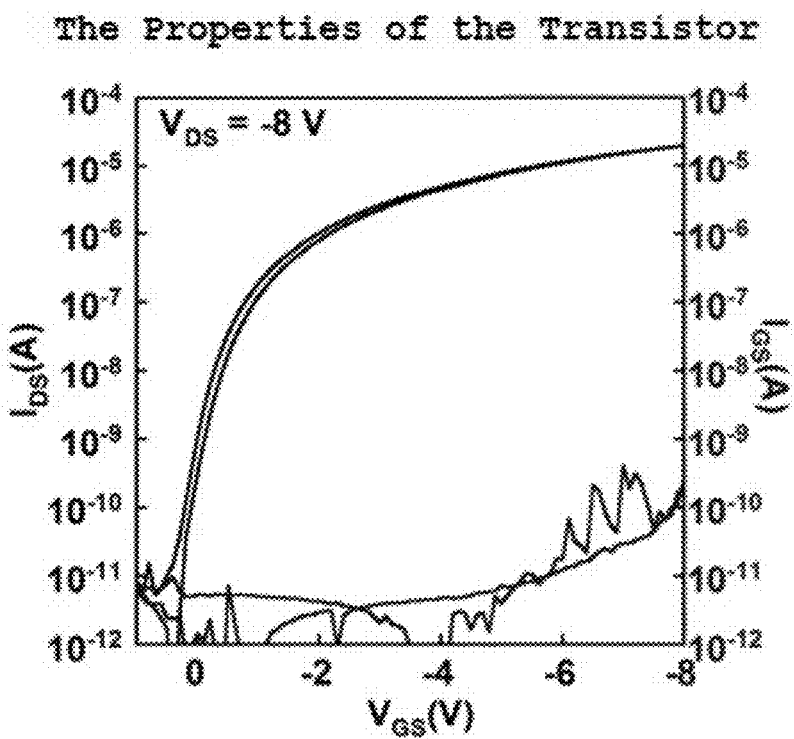

TRIPTYCENE DERIVATIVE USEFUL AS MATERIAL FOR FORMING SELF-ASSEMBLED FILM, METHOD FOR MANUFACTURING SAID TRIPTYCENE DERIVATIVE, FILM USING SAME, METHOD FOR MANUFACTURING SAID FILM, AND ELECTRONIC DEVICE USING SAID METHOD

TECHNICAL FIELD

The present invention relates to a triptycene derivative useful as a material for forming a self-assembled monolayer (SAM), a method for producing the triptycene derivative, a film using the triptycene derivatives, and a method for producing the film.

BACKGROUND ART

A self-assembled monolayer is referred to one that adsorb or chemically bind to a surface of a solid substrate and form a monomolecular layer (film) exhibiting high orientation due to interaction between the molecules. Incidentally, the self-assembled monolayer is also referred to as a self-organized monolayer or a self-integrated monolayer, but it is referred to as a self-assembled monolayer or simply a SAM film in the present specification.

The SAM film has been rapidly developed since it was reported that the SAM film formed on a glass substrate by using organosilane compounds (see Non-Patent Document 1) and also on a gold substrate by using organic sulfur compounds (see Non-Patent Document 2).

The SAM film is more stable than the LB (Langmuir-Blodgett) film and can be formed by a gas phase reaction, and its application range has been widened. In addition, the thickness of the SAM film is determined by the size (length) of the molecule and the angle of inclination thereof to the substrate, and it is possible to produce precisely and conveniently a film in a molecular level of about 1 nm. Generally, about 0.2 nm of a film thickness correspond to one methylene unit in an alkyl chain, and it is possible to produce accurately a monolayer having a desired film thickness by adjusting the length of the alkyl chain.

It is possible to modify the properties of the surface of a solid substrate by forming a SAM film. For example, in an organic field effect transistor (organic FET) in which silicon oxide is generally used as an insulating layer, it has been reported that a SAM film of organic silane compounds such as octadecyltrichlorosilane (OTS) formed on the silicon oxide imparts water repellency to the surface of the insulating layer. As a result, the adjacent (organic) semiconductor improves in crystallinity, and therefore the charge mobility thereof is increased. Accordingly, it is possible to control the hydrophilicity or hydrophobicity of a surface of a solid substrate by forming a SAM film on the surface of the solid substrate.

In addition, it is possible to impart a specific function to a surface of a solid substrate by introducing a functional group exhibiting functionality to moiety of molecules forming a SAM film. For example, it is possible to impart various functions such as electron transfer and oxidation-reduction reactions, catalysis, light-induced electron transfer, electrochemical luminescence, recognition of ions and molecules, biosensor, bio-molecular devices, and photovoltaic power generation and the like to a surface of a solid substrate by forming a SAM film. The application of a SAM film in these fields is expected.

For example, it has been reported that formation of a SAM film using alkylenethiol compounds which have an amino group as an end group to anchor a saccharide having an aldehyde moiety or a compound having a carboxyl group (see Patent Document 1), formation of a SAM film using alkylenethiol compounds which have an electron accepting functional group such as a cyano aryl group at an end group (see Patent Document 2), formation of a SAM film exhibiting ultraviolet resistance using alkylenethiol compounds which have a polyphenylene group at an end group (see Patent Document 3), formation of a SAM film having a rigid adamantane surface film structure using bis(adamantylmethyl)disulfide (see Patent Document 4), formation of a SAM film for lithography using compounds having an alkylene chain in the middle of which a functional group sensitive to a relatively long-wavelength light is introduced so that the film is able to be patterned with the light (see Patent Document 5), formation of a SAM film for a photovoltaic cell or a photocharge separating element using compounds obtained by binding a pyrrole ring-expanded porphyrin and a fullerene covalently (see Patent Document 6), and the like.

Meanwhile, a report that a SAM film is formed using triptycene derivatives is not found. However, there are reports about triptycene derivatives as follows, an organic EL material made from polymers or copolymers of triptycene (see Patent Document 7), a method for producing triptycenediamine which is a raw material for a polyimide resin and a polyamide resin (see Patent Document 8), a liquid crystal polymer composition using a compound that is generically called "iptycenes" obtained by linking between triptycenes (see Patent Document 9), a polyamide acid obtained by reacting triptycenetriamines, a polyimide resin obtained by heating the polyamide acid, and an optical part using the resin (see Patent Document 10), use of a triptycene ring as a component of a macrocyclic module which is a material for a nanofilm (see Patent Document 11), a method for optical resolution of triptycene derivatives using enzyme (see Patent Document 12), an insulating film and an electronic device containing polymers which are obtained by polymerizing triptycene derivatives having a plurality of triple bonds or double bonds as a polymerization unit (see Patent Document 13), triptycene derivatives for photoresist having at least one acid-dissociable dissolution-inhibiting group (see Patent Document 14), and a liquid crystal polymer composition using compounds which have triptycene-1,4-diyl groups (see Patent Document 15), and the like.

In addition, it has also been reported that triptycene derivatives substituted with 1, 2, 5, or 6 long-chain alkoxy groups are regularly aligned to form smectic liquid crystals (see Non-Patent Document 3), but it is not disclosed that three substituents are regularly aligned in the same direction and the triptycene derivatives are suitable as a SAM film-forming material.

The present inventors have found out that triptycene derivatives (Janus-type triptycene derivatives) in which three identical substituents regularly align in the same direction form a film as substituents of the derivatives align in the same direction and integrate. Furthermore, they have reported that the film formed in this manner is self-assembled and further treatment provide a self-assembled monolayer (see Patent Document 16).

CITATION LIST

Patent Document

Patent Document 1: JP 2002-363154 A
Patent Document 2: WO 2003-055853 A1

Patent Document 3: JP 2004-33824 A
Patent Document 4: JP 2004-315461 A
Patent Document 5: JP 2007-277171 A
Patent Document 6: JP 2012-111716 A
Patent Document 7: JP 2002-539286 A
Patent Document 8: JP 2004-359599 A
Patent Document 9: JP 2004-506791 A
Patent Document 10: JP 2006-1968 A
Patent Document 11: JP 2006-512472 A
Patent Document 12: JP 2006-187225 A
Patent Document 13: JP 2008-75047 A
Patent Document 14: JP 2008-308433 A
Patent Document 15: JP 2010-248467 A
Patent Document 16: PCT/JP2013/004952

Non-Patent Document

Non-Patent Document 1: Sagiv, J., J. Am. Chem. Soc., 102, 92-98 (1980)
Non-Patent Document 2: Nuzzo, R. G., et al., J. Am. Chem. Soc., 105, 4481-4483 (1983)
Non-Patent Document 3: S. Norves, J. Org. Chem., 1993, 58, 2414-2418

SUMMARY OF THE INVENTION

Problems to be Solved by the Invention

The present invention provides a novel Janus-type triptycene derivative that is represented by the following Formula [I] and useful as a material substance for a self-assembled film, in particular a self-assembled monolayer, and a method for producing the same.

In addition, the present invention provides a film-forming material containing Janus-type triptycene derivatives represented by the following Formula [I], a self-assembled film using Janus-type triptycene derivatives represented by the following Formula [I], a solid substrate having the film on its surface, and a method for producing the film.

Furthermore, the present invention provides a high-performance, highly homogeneous and highly stable electronic device by forming a uniform interface between an insulator and an organic semiconductor. The electronic device of the present invention has the uniform interface between the insulator and the organic semiconductor, thus the electronic device is able to reduce a noise level, and as a result, the electronic device is able to detect a weak signal, for example, a signal emanating from a living body with high sensitivity. Furthermore, the film to constitute the interface of the present invention is flexible, thus can be applied to a large area, and consequently a flexible large-area electronic device is provided by the present invention.

Means to Solving the Problems

The present inventors have studied to introduce several types of groups having functions regiospecifically and face-specifically into triptycene. Moreover, the present inventors have found out that, in a case of a triptycene derivative which has three identical substituents face-specifically on one side of triptycene and of which the substituent has a relatively long carbon chain, benzene rings arranged in a three-blade shape of the triptycene derivatives integrate in a nesting shape, and the substituents of the triptycene derivatives align in the same direction and integrate to form a film (See Patent Document 16).

However, in the case of using triptycene derivatives having three identical substituents on one side of triptycene, an annealing treatment is required for fairing the molecules of the integrated structure, and it is difficult to obtain a well-ordered integrated structure without an annealing treatment. The present inventors carried out various investigations to seek the reason for requiring an annealing treatment, and then they hypothesized that three identical substituents extending to the same direction caused steric hindrance to each other and this mutual steric hindrance made it difficult to obtain a well-ordered integrated structure. However, it has been difficult in terms of synthetic chemistry to introduce three different kinds of substituents into three substitutable places on one side of triptycene respectively. Nevertheless, the present inventors have succeeded in synthesis and thus in providing a novel Janus-type triptycene derivative represented by the following Formula [I], which has different kinds of substituents on one side of triptycene. Moreover, the integrated structure formed using the Janus-type triptycene derivatives represented by the following Formula [I] can form a well-ordered integrated structure without an annealing treatment. The present inventors have been obtained the results as expected, and thus the present invention has been completed.

Furthermore, the present inventors have found out that the well-ordered integrated structure formed on an insulating layer of an electronic device make it possible not only to provide a high-quality film that is uniform and excellent in stability regardless of the nature of material or the surface state of the insulating layer but also to give a layer having a function such as an organic semiconductor.

In other words, the present invention relates to a Janus-type triptycene derivative represented by the following Formula [I].

[Chemical Formula 1]

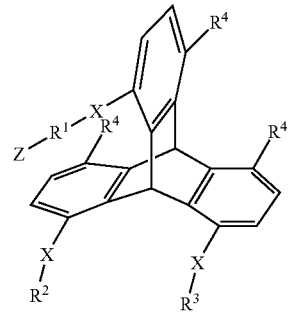

[I]

(In Formula [I], $R^1$ represents a divalent saturated or unsaturated hydrocarbon group having from 2 to 60 carbon atoms, wherein the hydrocarbon group may have at least one substituent, and at least one carbon atom in the hydrocarbon group may be substituted with an oxygen atom, a sulfur atom, a silicon atom, or $-NR^5-$ (here, $R^5$ represents a hydrogen atom, an alkyl group having from 1 to 10 carbon atoms, or an aryl group having from 6 to 30 carbon atoms);

$R^2$ represents a hydrogen atom or a saturated or unsaturated hydrocarbon group having from 1 to 4 carbon atoms;

$R^3$ represents a group $-R^1-Z$, a hydrogen atom, or a saturated or unsaturated hydrocarbon group having from 1 to 4 carbon atoms;

$R^4$ may be the same as or different from one another and each independently represents a hydrogen atom, a halogen atom, a hydroxyl group, a nitro group, a cyano group, an amino group, a monoalkyl-substituted amino group, a dialkyl-substituted amino group, an alkyl group which has from 1 to 10 carbon atoms and may have at least one substituent, an alkenyl group which has from 2 to 10 carbon atoms and may have at least one substituent, an alkynyl group which has from 2 to 10 carbon atoms and may have at least one substituent, an alkoxy group which has from 1 to 10 carbon atoms and may have at least one substituent, an alkylthio group which has from 1 to 10 carbon atoms and may have at least one substituent, a formyl group, an alkylcarbonyl group which has from 1 to 10 carbon atoms and may have at least one substituent, an alkoxycarbonyl group which has from 1 to 10 carbon atoms and may have at least one substituent, an alkylcarbonyloxy group which has from 1 to 10 carbon atoms and may have at least one substituent, an aryl group which has from 6 to 30 carbon atoms and may have at least one substituent, or a 5- to 8-membered heteroaryl group which has from 1 to 5 hetero atoms selected from the group consisting of nitrogen atom, oxygen atom, and sulfur atom and has from 2 to 10 carbon atoms and may have at least one substituent;

X represents a linker group consisting of a divalent atomic group which has from 1 to 5 atoms selected from the group consisting of nitrogen atom, oxygen atom, sulfur atom, carbon atom, and silicon atom and may have at least one hydrogen atom; and Z represents a hydrogen atom, a group capable of binding to or adsorbing on a surface of a solid substrate; or an end group consisting of a monovalent atomic group which has from 1 to 15 atoms selected from the group consisting of nitrogen atom, oxygen atom, sulfur atom, carbon atom, phosphorus atom, halogen atom, and silicon atom and may have at least one hydrogen atom.)

In addition, the present invention relates to a composition for a film-forming material comprising the Janus-type triptycene derivatives represented by Formula [I] described above.

Furthermore, the present invention relates to a film, in particular a self-assembled monolayer formed as the Janus-type triptycene derivatives represented by Formula [I] described above align in a self-assembled manner, and a structure having the film on a surface of a solid substrate.

In addition, the present invention relates to a method for producing a film of the Janus-type triptycene derivatives represented by Formula [I] described above on a surface of a solid substrate, and the method comprises, dissolving the Janus-type triptycene derivatives represented by Formula [I] described above in a solvent to obtain a solution, coating the solution on a surface of a solid substrate or immersing a solid substrate in the solution, drying the solid substrate, thereby the film is formed on the solid substrate, and further annealing the film formed on the dried substrate if necessary.

In addition, the present invention relates to a method for producing a structure having a film of the Janus-type triptycene derivatives represented by Formula [I] described above formed on a surface of a solid substrate, and the method comprises, dissolving the Janus-type triptycene derivatives represented by Formula [I] described above in a solvent to obtain a solution, coating the solution on a surface of a solid substrate or immersing a solid substrate in the solution, drying the solid substrate, thereby the film is formed on the solid substrate, and further annealing the film formed on the dried substrate if necessary.

Furthermore, the present invention relates to an electronic device including a film containing the Janus-type triptycene derivative represented by Formula [I] described above as a component.

The aspects of the present invention are as follows in more detail.

(1) A Janus-type triptycene derivative represented by Formula [I] described above.

(2) The Janus-type triptycene derivative according to (1), in which three groups $R^4$ in Formula [I] are all the same groups.

(3) The Janus-type triptycene derivative according to (1), in which three groups $R^4$ in Formula [I] are each different group.

(4) The Janus-type triptycene derivative according to any one of (1) to (3), in which X in Formula [I] is a divalent group represented by —$CH_2$—, —CH=CH—, —O—, or —$NR^6$— (here, $R^6$ represents a hydrogen atom or an alkyl group having from 1 to 4 carbon atoms).

(5) The Janus-type triptycene derivative according to (4), in which X in Formula [I] is a divalent group represented by —CH=CH— or —O—.

(6) The Janus-type triptycene derivative according to any one of (1) to (5), in which $R^1$ in Formula [I] is an alkylene group having from 2 to 30 carbon atoms, an alkenylene group having from 2 to 30 carbon atoms, an alkynylene group having from 2 to 30 carbon atoms, or a divalent arylene group which contains at least one aryl ring having from 6 to 30 carbon atoms and in which total carbon atoms are from 6 to 60.

(7) The Janus-type triptycene derivative according to (6), in which $R^1$ in Formula [I] is an alkylene group having from 2 to 30 carbon atoms or a divalent arylene group which contains at least one aryl ring having from 6 to 30 carbon atoms and in which total carbon atoms are from 6 to 60.

(8) The Janus-type triptycene derivative according to any one of (1) to (7), in which Z in Formula [I] is a hydrogen atom, a haloalkyl group having from 1 to 10 carbon atoms, an alkenyl group having from 2 to 10 carbon atoms, an alkynyl group having from 2 to 10 carbon atoms, a hydroxyl group, —$COOR^7$ (here, $R^7$ represents a hydrogen atom or an alkyl group which has from 1 to 5 carbon atoms and may have at least one substituent), —$N(R^8)_2$ (here, each of groups $R^8$ independently represents a hydrogen atom, an alkyl group which has from 1 to 5 carbon atoms and may have at least one substituent, or an aryl group which has from 6 to 30 carbon atoms and may have at least one substituent), or —$P(=O)(OR^{15})_2$ (here, each of groups $R^{15}$ independently represents a hydrogen atom, an alkyl group having from 1 to 10 carbon atoms, or an aryl group having from 6 to 12 carbon atoms).

(9) The Janus-type triptycene derivative according to (8), in which Z in Formula [I] is a hydrogen atom, —$CF_3$, —CH=$CH_2$, —C≡CH, —$COOR^7$ (here, $R^7$ represents a hydrogen atom or an alkyl group which has from 1 to 5 carbon atoms and may have at least one substituent), —$NH_2$, or —$N(Ar^1)_2$ (here, each of groups $Ar^1$ independently represents an aryl group which has from 6 to 30 carbon atoms and may have at least one substituent).

(10) The Janus-type triptycene derivative according to any one of (1) to (9), in which $R^2$ is an alkyl group having from 1 to 4 carbon atoms.

(11) The Janus-type triptycene derivative according to any one of (1) to (10), in which $R^3$ is a group —$R^1$—Z ($R^1$ and Z represent the groups described above).

(12) The Janus-type triptycene derivative according to any one of (1) to (10), in which $R^3$ is an alkyl group having from 1 to 4 carbon atoms.

(13) The Janus-type triptycene derivative according to any one of (1) to (12), in which $R^4$ in Formula [I] is a hydrogen atom, a halogen atom, a hydroxyl group, a nitro group, an alkoxy group which has from 1 to 10 carbon atoms and may have at least one substituent, or an aryl group which has from 6 to 30 carbon atoms and may have at least one substituent.

(14) The Janus-type triptycene derivative according to (13), in which $R^4$ in Formula [I] is a hydrogen atom, a halogen atom, or an alkoxy group which has from 1 to 10 carbon atoms and may have at least one substituent.

(15) A film formed as the Janus-type triptycene derivatives according to any one of (1) to (14) align in a self-assembled manner.

(16) The film according to (15), in which the Janus-type triptycene derivative has three benzene rings arranged in a three-blade shape as a skeletal structure and has three substituents on the same side of the skeletal structure, the benzene rings of the skeletal structures integrate in a nest shape, and the three substituents of the triptycene derivatives align in the same direction and integrate.

(17) The film according to (15) or (16), in which the film forms a layer structure composed of a portion in which the benzene rings arranged in a three-blade shape of the triptycene skeletal structures integrate in a nest shape and a portion in which substituents —X—$R^1$—Z of the triptycene derivatives represented by Formula [I] integrate.

(18) The film according to any one of (15) to (17), in which Z in Formula [I] is a polar functional group.

(19) The film according to the (18), in which the polar functional group is a hydroxyl group, an amino group, or a carboxyl group or an ester thereof.

(20) The film according to any one of (15) to (19), in which the film is a multilayer film.

(21) The film according to the (20), in which the film is a two-layer film.

(22) The film according to the (21), in which the two-layer film has a structure in which groups Z of the triptycene derivatives represented by Formula [I] face each other between molecules of each layer.

(23) The film according to any one of (15) to (19), in which the film is a monolayer.

(24) The film according to any one of (15) to (23), in which the film is a functional film.

(25) The film according to any one of (15) to (24), in which the film is formed on a surface of a solid substrate.

(26) A structure having the film according to any one of (15) to (25) on a surface of a solid substrate.

(27) The structure according to (26), in which the structure constitutes a part of an electronic device.

(28) The structure according to (27), in which the electronic device is a thin film transistor (TFT).

(29) The structure according to (26), in which the solid substrate comprise silicon oxide, glass, mica, an organic material, or a bio-derived material.

(30) A method for producing a film of Janus-type triptycene derivatives, the method comprising:
dissolving the Janus-type triptycene derivatives according to any one of (1) to (14) in a solvent to obtain a solution;
coating the solution on a surface of a solid substrate or immersing a solid substrate in the solution; and
drying the solid substrate, thereby the film is formed on the solid substrate.

(31) The method for producing the film according to (30), further comprising a step of annealing the film formed on the dried substrate.

(32) The method for producing the film according to (30) or (31), in which the solvent is a polar solvent.

(33) The method for producing the film according to (32), in which the polar solvent is dimethylformamide (DMF) or tetrahydrofuran (THF).

(34) The method for producing the film according to any one of (30) to (33), in which Z in Formula [I] is a polar functional group.

(35) The method for producing the film according to (34), in which the polar functional group is a hydroxyl group, an amino group, or a carboxyl group or an ester thereof.

(36) A method for producing a film of Janus-type triptycene derivatives, the method comprising:
heating the Janus-type triptycene derivatives according to any one of (1) to (14) to a melting point thereof or a higher temperature to evaporate, and
depositing the evaporated Janus-type triptycene derivatives on a solid substrate, thereby the film is formed on the solid substrate.

(37) The method for producing the film according to (36), further comprising a step of annealing the film formed on the substrate.

(38) The method for producing the film according to (37), in which the step of annealing is a heat treatment at a temperature from 100° C. to the melting point for from 5 to 50 minutes.

(39) The method for producing the film according to any one of (36) to (38), in which the step of depositing is conducted under a reduced pressure of from $10^{-5}$ Pa to $10^{-3}$ Pa.

(40) The method for producing the film according to any one of (36) to (39), in which X in Formula [I] is —O— and Z in Formula [I] is a hydrogen atom, —CH=$CH_2$, —C≡CH, or —$CF_3$.

(41) The method for producing the film according to (40), in which $R^1$ in Formula [I] is an alkylene group having from 8 to 15 carbon atoms.

(42) The method for producing the film according to (40) or (41), in which $R^1$ in Formula [I] is an alkylene group having from 9 to 12 carbon atoms.

(43) The method for producing the film according to any one of (30) to (42), in which the Janus-type triptycene derivative has three benzene rings arranged in a three-blade shape as a skeletal structure and has three substituents on the same side of the skeletal structure, the benzene rings of the skeletal structures integrate in a nest shape, and the three substituents of the triptycene derivatives align in the same direction and integrate.

(44) The method for producing the film according to any one of (30) to (43), in which the film forms a layer structure composed of a portion in which the benzene rings arranged in a three-blade shape of the triptycene skeletal structures integrate in a nest shape and a portion in which substituents —X—$R^1$—Z of the triptycene derivatives represented by Formula [I] integrate.

(45) The method for producing the film according to any one of (30) to (44), in which the film is a multilayer film.

(46) The method for producing the film according to (45), in which the film is a two-layer film.

(47) The method for producing the film according to (46), in which the two-layer film has a structure in which groups Z of the triptycene derivatives represented by Formula [I] face each other between molecules of each layer.

(48) The method for producing the film according to any one of (30) to (44), in which the film is a monolayer.

(49) The method for producing the film according to any one of (30) to (48), in which the film is a functional film.

(50) The method for producing the film according to any one of (30) to (49), in which the solid substrate comprises silicon oxide, glass, mica, an organic material, or a bio-derived material.

(51) A method for producing a structure having a film of Janus-type triptycene derivatives represented by Formula [I] formed on a surface of a solid substrate, the method comprising:

dissolving the Janus-type triptycene derivatives according to any one of (1) to (14) in a solvent to obtain a solution;

coating the solution on the surface of the solid substrate or immersing the solid substrate in the solution; and drying the solid substrate, thereby the film is formed on the solid substrate.

(52) The method for producing the structure according to (51), further comprising a step of annealing the film formed on the dried substrate.

(53) The method for producing the structure according to (51) or (52), in which the solvent is a polar solvent.

(54) The method for producing the structure according to (53), in which the polar solvent is dimethylformamide (DMF) or tetrahydrofuran (THF).

(55) The method for producing the structure according to any one of (51) to (54), in which Z in Formula [I] is a polar functional group.

(56) A method for producing a structure having a film of Janus-type triptycene derivatives represented by Formula [I] formed on a surface of a solid substrate, the method comprising:

heating the Janus-type triptycene derivatives according to any one of (1) to (14) to a melting point thereof or a higher temperature to evaporate, and depositing the evaporated Janus-type triptycene derivatives on the solid substrate, thereby the film is formed on the solid substrate.

(57) The method for producing the structure according to (56), further comprising a step of annealing the film formed on the substrate.

(58) The method for producing the structure according to (57), in which the step of annealing is a heat treatment at a temperature from 100° C. to a melting point for from 5 to 50 minutes.

(59) The method for producing the structure according to any one of (56) to (58), in which the step of depositing is conducted under a reduced pressure of from $10^{-5}$ Pa to $10^{-3}$ Pa.

(60) The method for producing the structure according to any one of (56) to (59), in which X in Formula [I] is —O— and Z in Formula [I] is a hydrogen atom, —CH=CH$_2$, —C≡CH, or —CF$_3$.

(61) The method for producing the structure according to (60), in which $R^1$ in Formula [I] is an alkylene group having from 8 to 15 carbon atoms.

(62) The method for producing the structure according to (60) or (61), in which $R^1$ in Formula [I] is an alkylene group having from 9 to 12 carbon atoms.

(63) The method for producing the structure according to any one of (51) to (62), in which the Janus-type triptycene derivative has three benzene rings arranged in a three-blade shape as a skeletal structure and has three substituents on the same side of the skeletal structure, the benzene rings of the skeletal structures integrate in a nest shape, and the three substituents of the triptycene derivatives align in the same direction and integrate.

(64) The method for producing the structure according to any one of (51) to (63), in which the film forms a layer structure composed of a portion in which the benzene rings arranged in a three-blade shape of the triptycene skeletal structure integrate in a nest shape and a portion in which substituents —X—$R^1$—Z of the triptycene derivatives represented by Formula [I] integrate.

(65) The method for producing the structure according to any one of (51) to (64), in which the film is a multilayer film.

(66) The method for producing the structure according to (65), in which the film is a two-layer film.

(67) The method for producing the structure according to (66), in which the two-layer film has a structure in which groups Z of the triptycene derivatives represented by Formula [I] face each other between molecules of each layer.

(68) The method for producing the structure according to any one of (51) to (64), in which the film is a monolayer.

(69) The method for producing the structure according to any one of (51) to (68), in which the film is a functional film.

(70) The method for producing the structure according to any one of (51) to (69), in which the solid substrate comprises silicon oxide, glass, mica, an organic material, or a bio-derived material.

The aspects of the present invention are as follows in more detail.

(71) An electronic device comprising a film formed as the Janus-type triptycene derivatives according to any one of (1) to (14) align in a self-assembled manner.

(72) The electronic device according to (71), comprising the film according to any one of (15) to (25).

(73) The electronic device according to (71) or (72), in which the electronic device is a transistor, a capacitor, a diode, a thyristor, an electroluminescent element, a sensor, or a memory.

(74) The electronic device according to (73), in which the electronic device is a transistor.

(75) The electronic device according to (73) or (74), in which the transistor is a thin film transistor.

(76) The electronic device according to (75), in which the thin film transistor is an organic thin film transistor comprising a gate electrode, a source electrode, a drain electrode, and a gate insulating layer on a substrate.

(77) The electronic device according to (76), in which the gate insulating layer comprises an insulating material and the film of the Janus-type triptycene derivatives represented by Formula [I].

(78) The electronic device according to (77), in which the gate insulating layer comprises the insulating material and the multilayer organic thin film.

(79) The electronic device according to (77) or (78), in which the insulating material of the gate insulating layer is an organic insulating material.

(80) The electronic device according to (79), in which the organic insulating material is polyimide, polymethylmethacrylate, and/or the Parylene (registered trademark).

(81) The electronic device according to any one of (77) to (80), in which the organic thin film of the Janus-type triptycene derivatives represented by Formula [I] comprises functional groups having functions of an organic semiconductor.

(82) The electronic device according to any one of (77) to (81), in which the thin film transistor further comprises a channel layer comprising a semiconductor.

(83) The electronic device according to (82), in which the semiconductor is an organic semiconductor.

(84) The electronic device according to (82) or (83), in which the channel layer is an organic semiconductor layer.

(85) The electronic device according to any one of (82) to (84), in which the organic thin film and the semiconductor of the channel layer are stacked in layers.

(86) The electronic device according to any one of (75) to (85), in which a boundary portion between the gate insulating layer and the organic semiconductor layer in the thin film transistor comprises the film according to any one of (15) to (25).

(87) The electronic device according to (86), in which the gate insulating layer, the organic thin film, and the organic semiconductor layer are stacked in layers.

(88) The electronic device according to (86) or (87), in which the groups —X—$R^1$—Z (referred to as first molecules) of the triptycene derivatives represented by Formula [I] are oriented to the insulator layer and the groups $R^2$ (referred to as second molecules) of the triptycene derivatives represented by Formula [I] are oriented to the organic semiconductor layer in the film.

(89) The electronic device according to any one of (75) to (88), in which the source electrode and/or the drain electrode of the thin film transistor is provided between the organic thin film and the channel layer.

(90) The electronic device according to (89), in which the channel layer is an organic semiconductor layer.

(91) The electronic device according to (73), in which the electronic device is a capacitor.

(92) The electronic device according to (91), in which the capacitor comprises a dielectric layer comprising the film according to any one of (15) to (25) between electrodes.

(93) The electronic device according to (92), in which the dielectric layer comprises a first dielectric and a second dielectric.

(94) The electronic device according to (93), in which the second dielectric is an organic dielectric.

(95) The electronic device according to (93) or (94), in which the organic thin film and the second dielectric are stacked in layers.

(96) A circuit board comprises the electronic device according to any one of (71) to (95) in an electronic circuit.

(97) The circuit board according to (96), in which the circuit board is a thin film circuit board.

(98) The circuit board according to (96) or (97), in which the circuit board comprises a thin film circuit board provided with a thin film transistor.

(99) The circuit board according to any one of (96) to (98), in which the circuit board comprises a pixel driving circuit for a display device such as a liquid crystal display device or an organic EL display device (so-called flat panel display).

(100) An electronic apparatus comprising the electronic device according to any one of (71) to (95) in the interior of the electronic apparatus.

(101) The electronic apparatus according to (100), in which the electronic apparatus is an electronic paper, an organic EL display, or a liquid crystal display.

(102) The electronic apparatus according to (100) or (101), in which the electronic apparatus is a medical electronic apparatus such as a cardiac potential measurement device, a myoelectric potential measurement device, or a brain potential measurement device.

(103) The electronic apparatus according to (100) or (101), in which the electronic apparatus is a television, a viewfinder type or monitor direct view type video tape recorder, a car navigation device, a pager, an electronic organizer, a calculator, an electronic newspaper, a word processor, a personal computer, a workstation, a video phone, a POS terminal, an apparatus having a touch panel, or the like.

(104) An organic thin film-forming composition comprising the Janus-type triptycene derivatives represented by Formula [I] according to any one of (1) to (14) and an organic thin film-forming carrier.

(105) The organic thin film-forming composition according to (104), in which the organic thin film is a SAM.

(106) The organic thin film-forming composition according to (104) or (105), in which the organic thin film-forming carrier is an organic solvent.

(107) The organic thin film-forming composition according to (106), in which the organic solvent is dimethylformamide (DMF) or tetrahydrofuran (THF).

Effects of the Invention

The present invention provides a novel film-forming material for forming a self-assembled film, in particular a self-assembled monolayer.

The self-assembled film of the conventional art is one in which the film-forming material binds to or adsorbs on a surface of a substrate and thus integrate. Therefore, the self-assembled film of the conventional art has to bind to or adsorb on the substrate surface. By contrast, the film-forming material of the present invention itself has the integrating ability and it thus does not necessarily have a functional group for binding or adsorbing to the surface of a substrate. In addition, triptycene itself has a rigid structure and the film of the triptycene derivatives has a regular arrangement in which benzene rings arranged three-blade shape of the triptycene skeletal structures integrate in a nest shape, and thus the substituents of the triptycene derivatives are regularly arranged with respect to the triptycene skeletal structure and become part of the film. Consequently, it is possible to form a regular and rigid film irrespective of the chemical and/or physical situations of the substrate surface.

In addition, it is possible to strengthen or weaken the interaction with a surface of a solid substrate by appropriately selecting the kind of the group Z in Formula [I] of the present invention. Furthermore, it is also possible to forma film having a two-layer structure similar to a biological film by selecting a group exhibiting affinity to one another as the groups Z or groups $R^4$.

As described above, a film formed by using the novel film-forming material of the present invention can exhibit unique properties different from those of the self-assembled film of the conventional art. The film can provide not only a thin film for an electronic device such as a thin film transistor but also a nanoscale thin film that has an extremely wide application range as a protective film, a film similar to a biological membrane, and the like.

Furthermore, the triptycene derivative of the present invention has two planes of a plane having the group —X—$R^1$—Z in Formula [I] and a plane of $R^4$ in Formula [I] on the upper and lower sides of the rigid triptycene skeletal structure, and it is thus possible to impart various kinds of functions simultaneously with the film-forming ability. For example, it is possible to adjust the hydrophilicity or hydrophobicity of one surface of the film appropriately by introducing an appropriate hydrophilic group or hydrophobic group into $R^4$ in Formula [I]. In addition, it is also possible to impart the properties of a semiconductor on one surface of the film by introducing a group such as an electron acceptor into $R^4$ in Formula [I].

The present invention provides a novel triptycene derivative for a novel film-forming material. The triptycene derivative of the present invention includes at least one of the group —X—$R^1$—Z in Formula [I] on only one plane of the rigid triptycene skeletal structure and a relatively small group such as a lower alkyl group in addition to the group —X—$R^1$—Z to eliminate the steric hindrance. Furthermore, the group —X—$R^1$—Z is constituted by three moieties having respective functions, the group $R^1$ is a long-chain group for obtaining the interaction required for film formation, and it is preferably a long-chain hydrophobic group and characterizes the properties of the film to be formed. The group X is a linker group for linking the group $R^1$ to the triptycene skeletal structure, and the group Z is an end group of the chain-like moiety and can function as a functional group if the interaction with a substrate or the like is necessary. Moreover, at least one of the three substituents is a relatively small group such as a lower alkyl group. Hence, the triptycene derivatives of the present invention not only can form a regular and stable thin film but also can eliminate the steric hindrance of the plane having the group —X—$R^1$—Z of the rigid triptycene skeletal structure. As a result, it is easy to forma stable thin film using the triptycene derivatives of the present invention and furthermore is extremely easy to modify the triptycene derivative according to the purpose of the thin film. The triptycene derivative of the present invention provide a film-forming material having a wide application range.

The use of the organic thin film of the present invention makes it possible to form an extremely homogeneous and clean interface between an organic semiconductor layer and an insulator layer, and it is thus possible to achieve an improvement in performance, homogeneity, and stability of an electronic device, in particular an organic thin film transistor. Furthermore, it is possible to form a uniform electronic device, in particular a transistor over a large area upon realizing a large-area flexible electronic device.

In addition, in another aspect of the present invention, both a molecular moiety which functions as a semiconductor and a molecular moiety which functions as an insulator are incorporated in one molecule, and the molecule forms a monolayer. One side of the monolayer can exhibit semiconductor properties, and the other side can form a layered structure of insulator layers. This makes it possible to form an extremely homogeneous boundary between a semiconductor and an insulator and thus to realize a transistor without disturbance at the interface. As the disturbance at the interface ultimately disappears, it is possible to fabricate a semiconductor element homogeneously and stably, therefore the element has the performance of high mobility, high durability and a low leakage current, which cannot be obtained by the technique of the related art.

Moreover, the structure of the monolayer of the present invention is defined by the geometric shape of the triptycene skeletal structure, and thus the resulting monolayer is not affected by the surface state of the lower layer or the upper layer substrate. This makes it possible to realize a high-performance electronic device combined with various substrates.

The electronic device of the present invention can realize an extremely high-performance flexible organic semiconductor device. As large-area flexible organic electronics can be applied to various kinds of displays, electronic paper or the like, the electronic device of the present invention can be employed not only to a personal computer, a portable terminal and home appliances but also to a medical field.

BRIEF DESCRIPTION OF DRAWINGS

FIG. 1 schematically illustrates a state in which Janus-type triptycene derivatives of the present invention integrate.

FIG. 2 schematically illustrates a single layer structure by Compound 1.

FIG. 3 schematically illustrates the crystal structure of 1,8,13-trimethoxytriptycene. The oxygen atom in the methoxy group is showed in red.

FIG. 4 is a photograph illustrating the result form measurement of the DNTT (dinaphthothienothiophene) film formed on the Parylene (registered trademark, paraxylylene-based resin) film by an atomic force microscope (AFM).

FIG. 5 is a photograph illustrating the result form measurement of the DNTT (dinaphthothienothiophene) film formed on the Compound 3 film formed on the Parylene (registered trademark, paraxylylene-based resin) film by an atomic force microscope (AFM).

FIG. 6 is a photograph illustrating the result form measurement of the DNTT (dinaphthothienothiophene) film formed on the Compound 4 film formed on the Parylene (registered trademark, paraxylylene-based resin) film by an atomic force microscope (AFM).

FIG. 7 illustrates the cross-sectional structure of a transistor manufactured by using the film of Compounds 4 of the present invention.

FIG. 8 is a graph illustrating the results form measurement of the DC bias stress resistance of the transistor of Example 5 using Compound 4 of the present invention and the transistor of Comparative Example 5.

FIG. 9 is a graph obtained by measuring the properties of the transistor of Example 5 using Compound 4 of the present invention.

DESCRIPTION OF EMBODIMENTS

Aspects of the present invention will be described in more detail.

"Triptycene" itself is a known compound and is a compound having benzene rings that are arranged in a unique three-blade shape. In the present invention, the position numbers in triptycene are as follows in conformity with the nomenclature by the CAS.

[Chemical Formula 2]

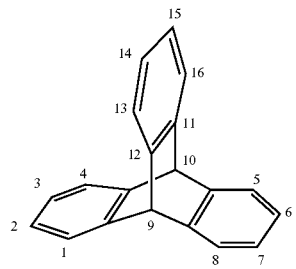

The "Janus-type triptycene derivative" in the present invention refers to a triptycene derivative in which two different planes of a plane on positions of 1, 8, and 13 and a plane on positions of 4, 5, and 16 have properties different from each other. Janus is the name of a god who appears in Roman mythology and has different faces in front and behind the head. The triptycene derivative of the present invention is named "Janus-type" based on the name of the god in Roman mythology since triptycene has two different planes of the plane on positions 1, 8, and 13 and the plane on positions of 4, 5, and 16.

Hence, it can be said that the Janus-type triptycene derivative of the present invention is a triptycene derivative having different properties on two planes of triptycene. The Janus-type triptycene derivative of the present invention is includes two planes of a plane that is involved in the formation of a film and a plane that is not involved in the formation of a film. In more detail, the Janus-type triptycene derivatives of the present invention include the same substituents for forming a film only on either plane, for example, the plane on positions of 1, 8, and 13. As an even more preferred aspect, an aspect is mentioned in which the three substituents of $R^4$ in Formula [I] of the Janus-type triptycene derivatives of the present invention are the same substituents and function as a plane having common properties, but the substituents on this plane are not required to be necessarily the same.

The present inventors have already provided a Janus-type triptycene derivative represented by the following formula (hereinafter, referred to as Compound 1) (see Patent Document 16).

[Chemical Formula 3]

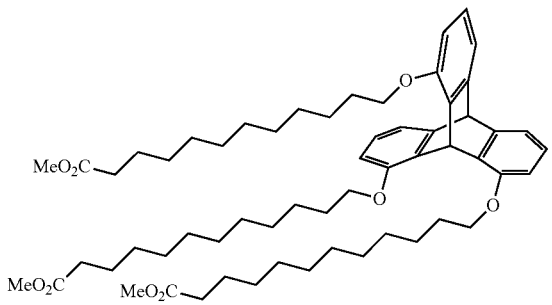

The phrase "benzene rings arranged in a three-blade shape of the triptycene skeletal structures integrate in a nest shape" in the present invention refers to a state in which each of the three benzene rings of the triptycene skeletal structure forms a face angle of 1200 and the benzene rings of adjacent triptycenes enter between the respective benzene rings in a nest shape, and FIG. 1 schematically illustrates such a state when viewed from the top.

FIG. 1 shows a state in which the benzene rings of adjacent triptycene skeletal structures enter between the respective benzene rings arranged in a three-blade shape of a triptycene skeletal structure and the triptycene skeletal structures regularly integrate. The distance from the bridgehead of triptycene to the bridgehead of adjacent triptycene was about 0.81 nm in a case in which Compounds 1 exemplified above integrate.

The "three identical substituents on the same side of the benzene rings of the triptycene skeletal structures align in the same direction and integrate" in the present invention refers to a state in which substituents of —X—$R^1$—Z present on one plane of the Janus-type triptycene derivatives represented by Formula [I] of the present invention extend to the same direction in the integrated triptycene skeletal structures having the benzene rings integrating in a nesting shape and the substituents of —X—$R^1$—Z align and integrate.

The state in which Compounds 1 exemplified above integrate is schematically illustrated in FIG. 2. The left side of FIG. 2 illustrates Compound 1, and the right side schematically illustrates a state in which Compounds 1 integrate in a layered form. The example shown in FIG. 2 is a state in which Compounds 1 integrate in four layers. The lower side of each triptycene layer indicates the integrated triptycene skeletal structures in which the benzene rings integrate in a nest shape. Moreover, three identical substituents on the same side of the triptycene layer, on the upper side in the case of Compound 1 of FIG. 2, align in the same direction and integrate to form a layer of alkylene which has an ester group at the end.

In a case where the substituents align randomly in different directions when the triptycene skeletal structures integrate, a film in perfect order as illustrated in FIG. 2 is not formed. Instead, a lump is formed. However, the present inventors first have found out that when the Janus-type triptycene derivatives of the present invention integrate substituents thereof do not align randomly but integrate in perfect order in the same direction to form a stable film. Thus, the present inventors have succeeded in forming a regular and stable nanoscale film.

The "film" in the present invention refers to an organic thin film formed by integrating the Janus-type triptycene derivatives of the present invention in the state described above. When a film formed by integrating in this manner is one layer, the film is a monolayer and can be referred to as a SAM. The film thickness can be regulated by the number of carbon atoms in the alkylene chain and can be determined in accordance with a general rule of being about 0.2 nm per one carbon atom.

In addition, it is also possible to form a multilayer film by stacking such a layer. In a multilayer film, there is a case in which the layers are stacked in the same direction or are stacked to face opposite directions. The state of stacking is determined depending on the kinds of the Z group and/or the $R^4$ group in Formula [I] or the conditions for film formation.

The film formed by coating a solution prepared by dissolving Compound 1 exemplified above in THF (1 mg/200 mL, about 5.3 µM) on a glass substrate and drying it may have a single-layer, a two-layer, or a three-layer structure. The film thickness in the single-layer structure was about 2.46 nm. The film thickness in the two-layer structure was about 5.4 nm. The film thickness in the three-layer structure was about 7.84 nm. In addition, the film formed by coating the same solution on a mica substrate and drying it may have a single-layer or a two-layer structure, and the film thickness in the single-layer structure was about 3.27 nm and the film thickness in the two-layer structure was about 6.45 nm. Furthermore, the film formed by coating the same solution on a mica substrate, drying it, and then annealing it at 180° C. has a single-layer structure, and the film thickness thereof was about 2.04 nm.

The "functional film" in the present invention refers to a film obtained by binding functional groups having various kinds of functions to the film of the present invention described above. In general, a film such as a SAM film is separated into three moieties which include a moiety for binding to or adsorbing on the surface of a solid substrate, a moiety for obtaining the van der Waals force between alkyl chains such as an alkyl chain to form a stable film, and the end moiety of the molecule. Moreover, it has been known that it is possible to impart various kinds of functions to the formed film by introducing a functional group having an electrochemical function, an optical function, a biological function and the like into the end moiety of the molecule for forming the film. As described above, it is possible to impart various kinds of functions to the film of the present invention by using the end moiety of the molecule in the same manner as the film of the related art.

As has been described above, the Janus-type triptycene derivative of the present invention has two planes of the "plane having the group —X—$R^1$—Z in Formula [I]" and the "plane of $R^4$ in Formula [I]", and it is possible to introduce functional groups having various functions into the plane of $R^4$ in the same manner as in the film of the related art. In addition, it is essential to have a moiety for binding to or adsorbing on a surface of a solid substrate in the film of the related art, but the moiety for binding to or adsorbing on a solid surface is not necessarily required in a film using the Janus-type triptycene derivative of the present invention. The reason is why the van der Waals force is exhibited between the alkyl chains such as an alkyl chain addition to the film forming ability of the triptycene skeletal structure moiety. Hence, it is also possible to introduce functional groups having various functions into the moiety of the group Z of the Janus-type triptycene derivative represented by Formula [I] of the present invention.

Consequently, the "functional film" in the present invention means a film formed by introducing functional groups having various kinds of functions into the plane that does not contribute to forming the film of the Janus-type triptycene derivatives of the present invention and/or into the moieties of the group Z of the Janus-type triptycene derivative represented by Formula [I] of the present invention.

As the "solid substrate" in the present invention, not only a solid substrate such as glass; quartz; sapphire; a nonmetal such as silicon or germanium; a nonmetal oxide such as silicon oxide; a metal such as gold, platinum, silver, or copper; a metal oxide such as indium oxide or Indium Tin Oxide (ITO); GaAs; or a solid substrate such as CdS, an organic substrate such as an organic polymer material such as polyolefin, polyacryl, polyethersulfone, polyimide, or polyethylene terephthalate; and a solid substrate such as a bio-derived material using a material derived from animals and plants such as collagen, starch, and cellulose as a raw material, which have been used as a solid substrate of a SAM film or the like in the conventional art, but also a solid that is hardly bound to or adsorbed on can be used as the substrate, and all the solids on which the film of the present invention that has been described above can stably exist can be included in the solid substrate. In addition, the shape of the solid is not particularly limited, and it may have a thin film shape.

The film using the Janus-type triptycene derivative of the present invention has not only the van der Waals force by the alkyl chain and the like but also film forming ability in the triptycene skeletal structure moiety, and it thus does not necessarily require the moiety for binding to or adsorbing on a surface of a solid substrate. Hence, it is not required to consider the binding properties or the adsorption ability with the solid substrate and the solid substrate is not particularly limited. However, it is preferable to select a Janus-type triptycene derivative containing a moiety capable of binding to and/or adsorbing on a solid substrate in order to secure positional stability of the film formed.

The "electronic device" in the present invention is a general term for electronic elements to do functional works such as amplification, data processing, and data transfer by applying the action of electrons. Examples of the typical "electronic device" may include an active element of a sensor such as a transistor, a diode, a thyristor, an organic EL, or a biosensor, but a passive element such as a resistor or a capacitor is also included in some cases. Examples of the electronic device in a preferred aspect of the present invention may include a transistor, in particular, a thin film transistor, and more preferably an organic field-effect transistor (OFET). The organic field-effect transistor (OFET) may be any of a bottom contact/top gate type, a bottom contact/bottom gate type, and a top contact/bottom gate type, but a top contact/bottom gate type is preferred.

The "electronic element" in the present invention is a general term for electronic components utilizing the electronic conduction in solid, includes an active element and a passive element. The electronic element of the present invention may be either an active element or a passive element, but is usually preferably an active element. In addition, the "electronic device" and the "electronic element" of the present invention are used as synonyms in a case where the electronic device is configured by a single electronic element.

The "circuit board" in the present invention refers to those in which an electronic circuit is formed on the surface of the solid substrate described above. The electronic circuit connects an electronic component to an electrical conductor, to create a path of current, and to allow the electric component to perform the intended operation. The electronic circuit can amplify a signal of interest, perform data processing such as calculation and control, or transfer data. The "circuit board" can have various sizes depending on the purpose. For example, the electronic circuit of the present invention may perform all of the input, processing, control, and output of data, or performs only one of the respective purposes.

The "electronic apparatus" in the present invention includes various kinds of electronic products equipped with at least one kind of the electronic device, electronic element, or circuit board that is described above, and examples thereof may include: electronic products for home use such as a television; a view finder type or monitor direct view type video tape recorder; a car navigation apparatus; an electronic notebook; an electronic calculator; an electronic newspaper; a word processor; a personal computer; a workstation; a TV phone; and a POS terminal, in particular, a display device of these electronic products, and electronic products for business use such as medical electronic apparatuses such as a cardiac potential measuring device, a muscle potential measuring device and a brain potential measuring device, in particular, a display device of these medical electronic apparatuses. In addition, the "electronic apparatus" of the present invention may be various kinds of devices constituting the electronic products described above, and examples of such a device may include a display device such as an electronic paper, an organic EL display, or a liquid crystal display, and a sensor device such as various kinds of sensors.

The "component" in the present invention refers to the part that is required to constitute the electronic devices or electronic elements described above and formed by materials having the same nature. For example, a layer such as an insulating layer or an organic thin film layer is mentioned as the example of the "component". In addition, including the "component" means that the electronic devices or electronic elements described above include the "component" therein, that is, the "component" is present as a part of the electronic devices or electronic elements described above.

The "divalent saturated or unsaturated hydrocarbon group having from 2 to 60 carbon atoms" in the present invention is a divalent saturated or unsaturated, chain or cyclic, and linear or branched hydrocarbon group having from 2 to 60, preferably from 2 to 30, and more preferably from 5 to 30 carbon atoms. These saturated carbon atoms, unsaturated carbon atoms, carbon atoms forming a chain, and carbon atoms forming a ring may be regularly or irregularly disposed. Examples of the "divalent saturated or unsaturated hydrocarbon group having from 2 to 60 carbon atoms" in the present invention may include a linear or branched alkylene group having from 2 to 60, preferably from 2 to 30, and more preferably from 5 to 20 carbon atoms; a linear or branched alkenylene group having from 2 to 60, preferably from 2 to 30, and more preferably from 2 to 20 carbon atoms; a linear or branched alkynylene group having from 2 to 60, preferably from 2 to 30, and more preferably from 2 to 20 carbon atoms; and a divalent arylene group which has from 6 to 60, preferably from 6 to 30 carbon atoms in total and contains a monocyclic, polycyclic, or condensed aryl ring having from 6 to 30, preferably from 6 to 20, and more preferably from 6 to 12 carbon atoms (the arylene group may have an alkylene group, an alkenylene group, or alkynylene group between an aryl ring and another aryl ring or at the end). The carbon-carbon double bond for forming an alkenylene group, the carbon-carbon triple bond for forming an alkynylene group, or an aryl ring for forming an arylene group may be regularly or irregularly disposed in a saturated alkylene group (including the end) or before and after an unsaturated carbon-carbon bond.

More specific examples thereof may include a $C_6$, $C_7$, $C_8$, $C_9$, $C_{10}$, $C_{11}$, $C_{12}$, $C_{13}$, $C_{14}$, $C_{15}$, $C_{16}$, or $C_{17}$ linear or branched and preferably linear alkylene group, an alkylene group in which one, two, or three carbon-carbon double bonds are regularly or irregularly disposed in the alkylene group (including the end) described above, an unsaturated alkylene group represented by —(—CH=CH—)n- (here, n represents an integer of 3, 4, 5, 6, 7, or 8), an alkylene group in which one, two, or three carbon-carbon triple bonds are regularly or irregularly disposed in the alkylene group (including the end) described above, an arylene group represented by -(-Ph-CH=CH—)m-Ph- (here, Ph represents a p-phenylene group and m represents an integer of 1, 2, 3, or 4), and the like.

The "divalent saturated or unsaturated hydrocarbon group having from 2 to 60 carbon atoms" in the present invention may optionally have one or more substituents, and examples of the "substituent" may include a substituent selected from the group consisting of a halogen atom; a hydroxyl group; an alkyl group having from 1 to 5 carbon atoms; an alkoxy group having from 1 to 5 carbon atoms; an alkyl group which has from 1 to 5 carbon atoms and is substituted with from 1 to 5 and preferably from 1 to 3 halogen atoms; an alkoxy group which has from 1 to 5 carbon atoms and is substituted with from 1 to 5 and preferably from 1 to 3 halogen atoms; an amino group; and an amino group substituted with one or two alkyl groups having from 1 to 5 carbon atoms.

The description that in the "divalent saturated or unsaturated hydrocarbon group having from 2 to 60 carbon atoms", "at least one carbon atoms in the hydrocarbon group may be optionally substituted with an oxygen atom, a sulfur atom, a silicon atom, or —$NR^5$— (here, $R^5$ represents a hydrogen atom, an alkyl group having from 1 to 10 carbon atoms, or an aryl group having from 6 to 30 carbon atoms)" in the present invention indicates that one or two more carbon atoms in the chain of carbon atoms represented by —C—C—C— may be substituted with another atom so as to form a chain, for example, —C—O—C—, —C—S—C—, —C—$SiH_2$—C— (hydrogen atoms binding to the silicon atom in the formula may be substituted with a halogen atom, an alkyl group having from 1 to 10 carbon atoms or an alkoxy group having from 1 to 10 carbon atoms), or —C—$NR^5$—C—. In such substitution with another atom, the order of the substitutions may be regular or irregular.

Examples of the "alkyl group having from 1 to 10 carbon atoms" in the present invention may include a linear or branched alkyl group having from 1 to 10 carbon atoms, preferably from 1 to 8 carbon atoms, and more preferably from 1 to 5 carbon atoms. Examples of such an alkyl group may include a methyl group, an ethyl group, an n-propyl group, an isopropyl group, an n-butyl group, an isobutyl group, a sec-butyl group, a tert-butyl group, a pentyl group, a hexyl group, and an octyl group.

Examples of the "alkyl group which has from 1 to 5 carbon atoms and may have at least one substituent" in the present invention may include a linear or branched alkyl group having from 1 to 5 carbon atoms, preferably from 1 to 4 carbon atoms, more preferably form 1 to 3 carbon atoms. Examples of such an alkyl group may include a methyl group, an ethyl group, an n-propyl group, an isopropyl group, an n-butyl group, an isobutyl group, a sec-butyl group, a tert-butyl group, and a pentyl group.

In addition, examples of the "saturated or unsaturated hydrocarbon group having from 1 to 4 carbon atoms" in the present invention may include an alkyl group, alkenyl group, or alkynyl group having from 1 to 4 carbon atoms. Preferred examples of the "saturated or unsaturated hydrocarbon group having from 1 to 4 carbon atoms" may include a linear alkyl group having from 1 to 4 carbon atoms and preferably from 1 to 2 carbon atoms, and examples thereof may include a methyl group, an ethyl group, an n-propyl group, and an n-butyl group.

Examples of the "alkenyl group having from 2 to 10 carbon atoms" in the present invention may include a linear or branched alkenyl group that is a group having one or more carbon-carbon double bonds and has from 2 to 10 carbon atoms in total, preferably from 2 to 8 carbon atoms in total, and more preferably from 2 to 6 carbon atoms in total. Examples of such an alkenyl group may include a vinyl group, a 1-methyl-vinyl group, a 2-methyl-vinyl group, an n-2-propenyl group, a 1,2-dimethyl-vinyl group, a 1-methyl-propenyl group, a 2-methyl-propenyl group, an n-1-butenyl group, an n-2-butenyl group, and an n-3-butenyl group.

Examples of the "alkynyl group having from 2 to 10 carbon atoms" in the present invention may include a linear or branched alkynyl group that is a group having one or more carbon-carbon triple bonds and has from 2 to 10 carbon atoms in total, preferably from 2 to 8 carbon atoms in total, and more preferably from 2 to 6 carbon atoms in total. Examples of such an alkynyl group may include an ethynyl group, an n-1-propynyl group, an n-2-propynyl group, an n-1-butynyl, an n-2-butynyl group, and an n-3-butynyl group.

Examples of the "aryl group having from 6 to 30 carbon atoms" in the present invention may include a monocyclic, polycyclic, or condensed aryl group having from 6 to 30 carbon atoms, preferably having from 6 to 18 carbon atoms, and more preferably from 6 to 12 carbon atoms. Examples of such a carbocyclic aromatic group may include a phenyl group, a naphthyl group, a biphenyl group, a phenanthryl group, and an anthryl group.

Examples of the "5- to 8-membered heteroaryl group which has from 1 to 5 heteroatoms selected from the group consisting of nitrogen atom, oxygen atom, and sulfur atom and has from 2 to 10 carbon atoms" in the present invention may include a monocyclic, polycyclic, or condensed heteroaryl group which contains from 1 to 5, preferably from 1 to 3 or from 1 to 2 heteroatoms selected from the group consisting of nitrogen atom, oxygen atom, and sulfur atom and has a 5- to 8-membered ring and preferably a 5- to 6-membered ring. Examples of such a heterocyclic group may include a 2-furyl group, a 2-thienyl group, a 2-pyrrolyl group, a 2-pyridyl group, a 2-indole group, and a benzimidazolyl group.

Examples of the "alkoxy group having from 1 to 10 carbon atoms" in the present invention may include a group in which an oxygen atom binds to the above-described alkyl group having from 1 to 10 carbon atoms. Examples of such an alkoxy group may include a methoxy group, an ethoxy group, an n-propoxy group, an isopropoxy group, a butoxy group, and a pentyloxy group.

Examples of the "alkylthio group having from 1 to 10 carbon atoms" in the present invention may include a group in which a sulfur atom binds to the above-described alkyl group having from 1 to 10 carbon atoms. Examples of such an alkylthio group may include a methylthio group, an ethylthio group, an n-propylthio group, an isopropylthio group, a butylthio group, and a pentylthio group. The sulfur atom in these alkylthio groups may be sulfinyl (—SO—) or sulfonyl (—$SO_2$—).

Examples of the "alkylcarbonyl group having from 1 to 10 carbon atoms" in the present invention may include a group in which a carbonyl group (—CO— group) binds to the above-described alkyl group having from 1 to 10 carbon atoms. Examples of such an alkylcarbonyl group may include a methylcarbonyl group, an ethylcarbonyl group, an n-propylcarbonyl group, and an isopropylcarbonyl group.

Examples of the "alkoxycarbonyl group having from 1 to 10 carbon atoms" in the present invention may include a group in which an oxycarbonyl group (—O—CO— group) binds to the above-described alkyl group having from 1 to 10 carbon atoms. Examples of such an alkoxycarbonyl group may include a methoxycarbonyl group, an ethoxycarbonyl group, an n-propoxycarbonyl group, and an isopropoxycarbonyl group.

Examples of the "alkylcarbonyloxy group having from 1 to 10 carbon atoms" in the present invention may include a group in which a carbonyloxy group (—CO—O— group) binds to the above-described alkyl group having from 1 to 10 carbon atoms. Examples of such an alkylcarbonyloxy group may include a methylcarbonyloxy group, an ethylcarbonyloxy group, an n-propylcarbonyloxy group, and an isopropylcarbonyloxy group.

The "substituent" in the various kinds of groups in the present invention is not particularly limited, but examples thereof may include a halogen atom, a hydroxyl group, a nitro group, a cyano group, a substituted or unsubstituted amino group, an alkylsilyl group, an alkyl group having from 1 to 10 carbon atoms, an alkenyl group having from 2 to 10 carbon atoms, an alicyclic hydrocarbon group having from 3 to 10 carbon atoms, an aryl group having from 6 to 30 carbon atoms, an arylalkyl group having from 7 to 30 carbon atoms, a heteroaryl group, an alkylcarbonyl group having from 1 to 10 carbon atoms, an alicyclic hydrocarboncarbonyl group having from 3 to 16 carbon atoms, an arylcarbonyl group having from 6 to 30 carbon atoms, an arylalkylcarbonyl group having from 7 to 30 carbon atoms, an alkoxy group having from to 10 carbon atoms, an alkylcarbonyloxy group having from 1 to 10 carbon atoms, an arylcarbonyloxy group having from 7 to 30 carbon atoms, an arylalkylcarbonyloxy group having from 7 to 30 carbon atoms, an alkoxycarbonyl group having from 2 to 21 carbon atoms, a carbocyclic aromatic-oxycarbonyl group having from 7 to 37 carbon atoms, an aryloxycarbonyl group having from 6 to 30 carbon atoms, and an arylalkyloxycarbonyl group having from 7 to 30 carbon atoms.

The "monoalkyl-substituted amino group" in the present invention is an amino group in which one hydrogen atom in the amino group (—$NH_2$) is substituted with the above-described alkyl group having from 1 to 10 carbon atoms, and examples thereof may include a methylamino group and an ethylamino group.

The "dialkyl-substituted amino group" in the present invention is an amino group in which two hydrogen atoms in the amino group (—$NH_2$) are substituted with the above-described alkyl group having from 1 to 10 carbon atoms, respectively, and examples thereof may include a dimethylamino group, a diethylamino group, and a methylethylamino group.

The "formyl group" in the present invention is an aldehyde group (—CHO).

Examples of the "halogen atom" in the present invention may include fluorine atom, chlorine atom, bromine atom, or iodine atom.

The "trialkylsilyl group" in the present invention is a silyl group substituted with three of the above-described alkyl group having from 1 to 5 carbon atoms, and the respective alkyl groups may be the same as or different from one another. Examples of such a trialkylsilyl group may include a triethylsilyl group, an ethyldimethylsilyl group, a tert-butyldimethylsilyl group, and a tert-butyldiethylsilyl group.

The "linker group consisting of a divalent atomic group which has from 1 to 5 atoms selected from the group consisting of nitrogen atom, oxygen atom, sulfur atom, carbon atom, and silicon atom, and may have at least one hydrogen atoms" in the divalent linker group X of Formula [I] of the present invention is a group consisting of a divalent atomic group composed of from 1 to 5 atoms selected from the group consisting of nitrogen atom, oxygen atom, sulfur atom, carbon atom, and silicon atom other than hydrogen atom, and may have at least one hydrogen atom, and is a group to link the triptycene skeletal structure with the group $R^1$ of a divalent hydrocarbon group. The structure of the linker group is not particularly limited. Preferred examples of the group X may include —O—; —S—; —SO—; —$SO_2$—; —$NR^6$— (here, $R^6$ represents a hydrogen atom or an alkyl group having from 1 to 4 carbon atoms); —$CH_2$—; —$CH_2$—$CH_2$—; —CH=CH—; —$C_6H_4$— (phenylene group); —$C_4H_2S$— (divalent thiophene); —CO—; —OCO—; —COO—; —OCOO—; —$CONR^{61}$— (here, $R^{61}$ represents a hydrogen atom or an alkyl group having from 1 to 3 carbon atoms); —$NR^{62}CO$— (here, $R^{62}$ represents a hydrogen atom or an alkyl group having from 1 to 2 carbon atoms); —NHCONH—, —CO—$NR^{63}$—$NR^{63}$— (here, $R^{63}$ each independently represent a hydrogen atom or a methyl group); —$SiR^9R^{10}$—O— (here, $R^9$ and $R^{10}$ each independently represent a hydrogen atom, an alkyl group having from 1 to 3 carbon atoms, an alkoxy group having from 1 to 3 carbon atoms, or an amino group which may be substituted with an alkyl group having from 1 to 3 carbon atoms); —O—$SiR^9R^{10}$—O— (here, $R^9$ and $R^{10}$ each independently represent a hydrogen atom, an alkyl group having from 1 to 3 carbon atoms, an alkoxy group having from 1 to 3 carbon atoms, or an amino group which may be substituted with an alkyl groups having from 1 to 3 carbon atoms); —$SiR^9R^{10}$—NH— (here, $R^9$ and $R^{10}$ each independently represent a hydrogen atom, an alkyl group having from 1 to 3 carbon atoms, an alkoxy group having from 1 to 3 carbon atoms, or an amino group which may be substituted with an alkyl groups having from 1 to 3 carbon atoms); and —NH—SiR$^9$R$^{10}$—O— (here, R$^9$ and R$^{10}$ each independently represent a hydrogen atom, an alkyl group having from 1 to 3 carbon atoms, an alkoxy group having from 1 to 3 carbon atoms, or an amino group which may be substituted with an alkyl groups having from 1 to 3 carbon atoms).

Preferred examples of the group X in Formula [I] may include —O—; —S—; —SO—; —SO$_2$—; —NR$^6$— (here, R$^6$ represents a hydrogen atom or an alkyl group having from 1 to 4 carbon atoms); —CH$_2$—; —CH═CH—; —CO—; —OCO—; —CONR$^{61}$— (here, R$^6$ represents a hydrogen atom or an alkyl group having from 1 to 3 carbon atoms); and —NR$^{62}$CO— (here, R$^{62}$ represents a hydrogen atom and or an alkyl group having from 1 to 2 carbon atoms), and particularly preferred examples of the group X may include —O—; —NR$^6$— (here, R$^6$ represents a hydrogen atom or an alkyl group having from 1 to 4 carbon atoms); —CH$_2$—; and —CO—.

The "group capable of binding to or adsorbing on a surface of a solid substrate" in the end group Z in Formula [I] of the present invention is a functional group that can bind to or adsorb on a surface of a substrate such as glass, metal, or metal oxide. Examples thereof may include a trimethoxysilyl group or a trichlorosilyl group with respect to a glass substrate, and a group containing a sulfur atom such as a mercapto group or a disulfide group with respect to gold.

The "end group consisting of a monovalent atomic group which has from 1 to 15 atoms selected from the group consisting of nitrogen atom, oxygen atom, sulfur atom, carbon atom, phosphorus atom, halogen atom, and silicon atom, and may have at least on hydrogen atom" in the end group Z in Formula [I] of the present invention is a monovalent group to be the end of the group R$^1$ of a divalent hydrocarbon group in Formula [I] of the present invention. It is not particularly limited as long as it is a monovalent atomic group composed of from 1 to 15, preferably from 1 to 10, and more preferably from 1 to 6 atoms and one or more hydrogen atoms if necessary. Preferred examples of the group Z may include an alkyl group having from 1 to 10 carbon atoms; a linear or branched alkenyl group having from 2 to 15, preferably from 2 to 10, and more preferably from 2 to 6 carbon atoms; a linear or branched alkynyl group having from 2 to 15, preferably from 2 to 10, and more preferably from 2 to 6 carbon atoms; a divalent aryl group which has from 6 to 15, and preferably from 6 to 12 carbon atoms in total and contains a monocyclic, polycyclic, or condensed aryl ring having from 6 to 15, preferably from 6 to 12, and more preferably 6 to 10 carbon atoms (the aryl group may have an alkylene group, an alkenylene group, or an alkynylene group between an aryl ring and another aryl ring or at the end); a haloalkyl group having from 1 to 10 carbon atoms in which any position of an alkyl group having from 1 to 10 carbon atoms is substituted with from 1 to 7 halogen atoms; —OR$^{11}$ (here, R$^1$ represents a hydrogen atom or an alkyl group having from 1 to 10 carbon atoms); —SR$^{11}$ (here, R$^{11}$ represents a hydrogen atom or an alkyl group having from 1 to 10 carbon atoms); —SOR$^{11}$ (here, R$^{11}$ represents a hydrogen atom or an alkyl group having from 1 to 10 carbon atoms); —SO$_2$R$^{11}$ (here, R$^{11}$ represents a hydrogen atom or an alkyl group having from 1 to 10 carbon atoms); —N(R$^{12}$)$_2$ (here, R$^{12}$'s each independently represent a hydrogen atom, an alkyl group having from 1 to 10 carbon atoms or an aryl group having from 6 to 12 carbon atoms); —CO—R$^{13}$ (here, R$^{13}$ represents a hydrogen atom, an alkyl group having from 1 to 10 carbon atoms or an aryl group having from 6 to 12 carbon atoms); —OCO—R$^3$ (here, R$^{13}$ represents a hydrogen atom, an alkyl group having from 1 to 10 carbon atoms or an aryl group having from 6 to 12 carbon atoms); —COO—R$^{13}$ (here, R$^{13}$ represents a hydrogen atom, an alkyl group having from 1 to 10 carbon atoms or an aryl group having from 6 to 12 carbon atoms); —OCOO—R$^{14}$ (here, R$^{14}$ represents an alkyl group having from 1 to 10 carbon atoms or an aryl group having from 6 to 12 carbon atoms); —CON(R$^{13)\,2}$ (here, R$^{13}$'s each independently represent a hydrogen atom, an alkyl group having from 1 to 10 carbon atoms or an aryl group having from 6 to 12 carbon atoms); —NR$^{13}$CO—R$^{13}$ (here, R$^{13}$'s each independently represent a hydrogen atom, an alkyl group having from 1 to 10 carbon atoms or an aryl group having from 6 to 12 carbon atoms); —N(R$^{13}$)CON(R$^{13}$)$_2$ (here, R$^{13}$'s each independently represent a hydrogen atom, an alkyl group having from 1 to 10 carbon atoms or an aryl group having from 6 to 12 carbon atoms); —CO—NR$^{13}$—N(R$^{13}$)$_2$ (here, R$^{13}$'s each independently represent a hydrogen atom, an alkyl group having from 1 to 10 carbon atoms or an aryl group having from 6 to 12 carbon atoms); —SiR$^9$R$^{10}$—O—R$^{13}$ (here, R$^9$ and R$^{10}$ each independently represent a hydrogen atom, an alkyl group having from 1 to 3 carbon atoms, an alkoxy group having from 1 to 3 carbon atoms, or an amino group which may be substituted with one or more alkyl groups having from 1 to 3 carbon atoms, and R$^{13}$ represents a hydrogen atom, an alkyl group having from 1 to 10 carbon atoms or an aryl group having from 6 to 12 carbon atoms); —O—SiR$^9$R$^{10}$—O—R$^{13}$ (here, R$^9$ and R$^{10}$ each independently represent a hydrogen atom, an alkyl group having from 1 to 3 carbon atoms, an alkoxy group having from 1 to 3 carbon atoms, or an amino group which may be substituted with one or more alkyl group having from 1 to 3 carbon atoms, and R$^3$ represents a hydrogen atom, an alkyl group having from 1 to 10 carbon atoms or an aryl group having from 6 to 12 carbon atoms); —SiR$^9$R$^{10}$—N(R$^{13}$)$_2$ (here, R$^9$ and R$^{10}$ each independently represent a hydrogen atom, an alkyl group having from 1 to 3 carbon atoms, an alkoxy group having from 1 to 3 carbon atoms, or an amino group which may be substituted with one or more alkyl group having from 1 to 3 carbon atoms, and R$^{13}$ represents a hydrogen atom, an alkyl group having from 1 to 10 carbon atoms or an aryl group having from 6 to 12 carbon atoms); —NH—SiR$^9$R$^{10}$—O—R$^{13}$ (here, R$^9$ and R$^{10}$ each independently represent a hydrogen atom, an alkyl group having from 1 to 3 carbon atoms, an alkoxy group having from 1 to 3 carbon atoms, or an amino group which may be substituted with one or more alkyl group having from 1 to 3 carbon atoms, and R$^{:3}$ represents a hydrogen atom, an alkyl group having from 1 to 10 carbon atoms or an aryl group having from 6 to 12 carbon atoms); —P(OR$^{15}$)$_2$ (here, R$^{15}$'s each independently represent a hydrogen atom, an alkyl group having from 1 to 10 carbon atoms or an aryl group having from 6 to 12 carbon atoms); and —P(═O)(OR$^{15}$)$_2$ (here, R$^{15}$'s each independently represent a hydrogen atom, an alkyl group having from 1 to 10 carbon atoms or an aryl group having from 6 to 12 carbon atoms).

The "Janus-type triptycene derivative" of Formula [I] of the present invention is a triptycene derivative which has two different planes of the plane on positions of 1, 8, and 13 and the plane on positions of 4, 5, and 16 and of which the two different planes have properties different from each other. In Non-Patent Document 3, a triptycene derivative is produced by the Diels-Alder reaction using benzoquinone as a key reaction, but it is difficult to produce the "Janus-type triptycene derivative" of the present invention by this method since the same substituent (—OH) is simultaneously introduced into the 13-position and the 16-position.

The present inventors have succeeded in producing a three substituted triptycene derivative by conducting the condensation of 1,8-dialkoxyanthracene with a compound in which a phenolic hydroxyl group of 1-alkoxy-6-trialkylsilylphenol is set as the leaving group by a triflate group in the presence of a condensing agent. A specific example of this reaction is presented in Example 1 to be described later. It is possible to produce a three substituted triptycene derivative by this method, but the three substituted triptycene derivative thus produced is a mixture of a 1,8,13-three substituted triptycene derivative (Janus type) and a 1,8,16-three substituted triptycene derivative (non-Janus type). It is difficult to separate the mixture, but the present inventors have succeeded in separating and purifying the 1,8,13-trimethoxytriptycene by purifying this through recrystallization. See Example 1 to be described later.

The 1,8,13-trimethoxytriptycene can be separated and purified as a crystal having a unique packing structure in which the benzene rings arranged in a three-blade shape of the triptycene moiety integrate in a nest shape. The crystal structure of 1,8,13-trimethoxytriptycene is illustrated in FIG. 3. In FIG. 3, the oxygen atom of the methoxy group is shown in red. This crystal structure has an integrated structure in which the dipole is offset between the layer of triptycene molecules having a methoxy group facing the back side of the paper and the layer of triptycene molecules having a methoxy group facing the front side of the paper. Surprisingly, such a nest-shaped crystal structure is not seen in unsubstituted triptycene. It is demonstrated in this crystal structure that the characteristic integrated structure is brought about by the substituent structure of the Janus-type molecule of the present invention furnished with directionality.

Crystal form is an orthorhombic crystal system, and the values of a, b, and c of this crystal form are 15.608, 13.388, and 8.041, respectively, in a unit of angstrom. The value of V is 1680 cubic angstrom.

As described above, the present inventors first have succeeded in producing a "Janus-type triptycene derivative" having the same substituent in one direction of the triptycene skeletal structure.

The 1,8,13-trimethoxytriptycene that is separated and purified in this manner can be converted into 1,8,13-trihydroxytriptycene through hydrolysis by a usual method. For example, 1,8,13-trimethoxytriptycene can be hydrolyzed in a solvent such as dichloromethane in the presence of a boron halide.

Moreover, it is possible to produce the "Janus-type triptycene derivative" of the present invention by various kinds of known synthetic means using 1,8,13-trimethoxytriptycene and 1,8,13-trihydroxytriptycene obtained by the hydrolysis thereof as the key intermediate.

For example, they can be converted into a monoalkoxy derivative or a dialkoxy derivative through alkylation using an alkylating agent. They can further be converted into the Janus type triptycene derivative having different substituents of the present invention through alkylation, for example, methylation or ethylation of the remaining one or two hydroxyl groups. Alternatively, they can be converted into an ester derivative by various kinds of carboxylic acids or sulfonic acids. In this case, one or two hydroxyl groups can be esterified by selecting the reaction conditions. Furthermore, they can be converted into 1,8,13-tricyanotriptycene by converting the hydroxyl group into triflate (Tf: trifluoromethanesulfonate) and then cyanating with zinc dicyanide. The cyano group can be converted into a formyl group or a carboxyl group through hydrolysis by a usual method. Alternatively, the cyano group can be converted into an aminomethyl group through reduction by a usual method, and the amino group can be substituted with various kinds of substituents by a usual method.

In addition, the formyl group thus obtained can be used as various kinds of reaction raw materials as a carbonyl compound. For example, the formyl group can be converted into a —CH=C— bond through a reaction with a Wittig reagent. This can be converted into a carbon-carbon triple bond through dehydrogenation by a usual method.

In these reactions, only one or two functional groups can be selected and subjected to the reaction by selecting the reaction conditions.

Furthermore, it is possible to produce 4,5,16-tribromo-1,8,13-trihydroxytriptycene by the bromination of 1,8,13-trihydroxytriptycene using NBS (N-bromosuccinimide). This compound has different substituents on each side of the symmetry plane in the triptycene molecule. The compound has three hydroxyl groups on one side and three bromo groups on the other side of the symmetry plane. The compound is a key intermediate of the "Janus-type triptycene derivative" of the present invention having different groups having functions with respect to one symmetry plane.

This bromo-containing derivative can be directly converted into various kinds of aryl groups or heteroaryl groups such as a phenyl group or a thienyl group through various kinds of coupling reactions using a boron compound or a silicon compound. For example, in the case of attempting to introduce a group having a function to be an electron acceptor on the side where the bromo group is substituted, the group having a function can be introduced directly or stepwise by such coupling reactions.

For example, it is possible to produce 1,8-didodecyloxy-13-methoxytriptycene (hereinafter, this compound is referred to as "Compound 4") by methylating one hydroxyl group of 1,8,13-trihydroxytriptycene to obtain 1,8-dihydroxy-13-methoxytriptycene and reacting dodecyl bromide ($C_{12}H_{25}$—Br) with this in the presence of a base. The chemical reaction formula for this is presented below.

[Chemical Formula 4]

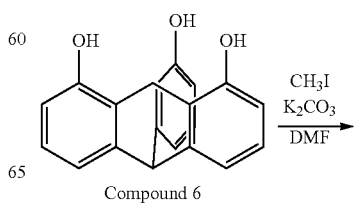

Compound 6

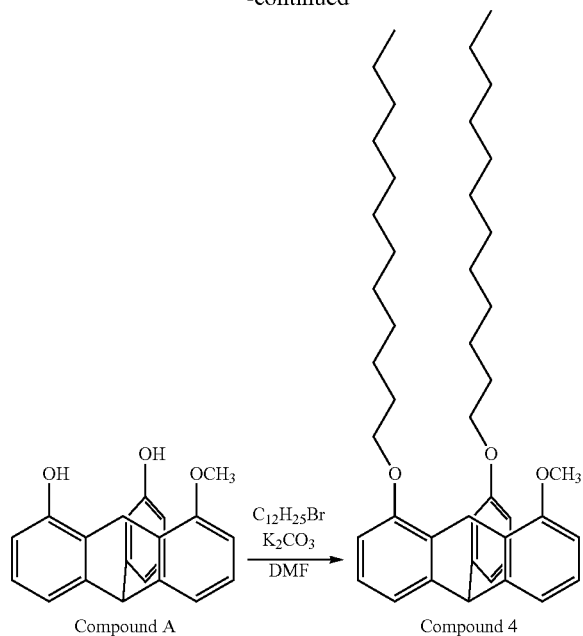

Compound 4 was vacuum-deposited on a silicon thin film having a thickness of 50 nm and the crystal state thereof was investigated by X-ray diffraction.

For comparison, 1,8,13-tridodecyloxytriptycene (hereinafter referred to as "Compound 3") was vacuum-deposited in the same manner.

A sharp X-ray reflection peak was obtained in the case of Compound 4, but only a broad X-ray reflection peak was obtained in the case of Compound 3. Each of them were subjected to the annealing treatment for 1 hour at 120° C., as a result, a significant change was not observed in the X-ray reflection peak of Compound 4 but a sharp X-ray reflection peak was obtained in the case of Compound 3. As described above, a significantly sharp peak is obtained in the case of the compound of the present invention even without an annealing treatment, but a sharp X-ray reflection peak is obtained for the first time after an annealing treatment in the case of Compound 3 having three identical substituents, and thus Compound 3 requires an annealing treatment. In contrast, an extremely sharp X-ray reflection peak was obtained in Compound 4 having only two large substituents of the present invention even without an annealing treatment.

Next, a change in $d_{001}$ and $d_{110}$ before and after the annealing treatment was measured.

In Compound 4 of the present invention, $d_{001}$ nearly unchanged from 2.11 nm to 2.05 nm by the annealing treatment, and a change was not observed as $d_{110}$ was 0.41 nm before and after the annealing treatment. In contrast, in Compound 3 having three identical substituents, $d_{001}$ significantly changed from 2.13 nm to 2.30 nm and $d_{110}$ changed from 0.41 nm to 0.40 nm by the annealing treatment.

As is apparent from the above, the compound represented by Formula [I] of the present invention can easily form a thin film exhibiting superior regularity as it has a small substituent in at least one among three substitutable places on the plane on positions of 1, 8, and 13 of triptycene. The factor for this is not necessarily clear, but it is considered that the steric hindrance is eliminated as at least one of the three places is smaller and formation of a thin film exhibiting excellent regularity is thus facilitated. Moreover, it is considered that the remaining one or two substituents on the plane on positions of 1, 8, and 13 are relatively long-chain substituents and it is thus possible to form a unique packing structure in which the benzene rings arranged in a three-blade shape of the triptycene moiety integrate in a nest shape and to form a unique film in the same manner as in the triptycene derivative which has three identical substituents on the plane on positions of 1, 8, and 13 and has been previously reported.

Next, the state of DNTT (dinaphthothienothiophene) in two case was observed through an AFM. In a case, poly-paraxylylene (Parylene (registered trademark)), which was one kind of organic insulating materials, was coated on a silicon substrate and DNTT of an organic semiconductor is deposited thereon. In another case, the Janus-type triptycene derivative was coated on the Parylene on a silicon substrate and DNTT was deposited thereon. In other words, the case of silicon substrate-Parylene layer-DNTT and the case of
silicon substrate-Parylene layer-Janus-type triptycene derivative layer-DNTT were compared to each other.

As the Janus-type triptycene derivative, "Compound 4" of the present invention described above was used. In addition, 1,8,13-tridodecyloxytriptycene (Compound 3) in which three substituents are all the same dodecyloxy group was used for comparison.

The results of the state of DNTT in the respective cases observed through an AMF are illustrated in FIG. 4, FIG. 5, and FIG. 6. FIG. 4 is an image of DNTT taken by an AMF in the case of not having a Janus-type triptycene derivative layer, FIG. 5 is an image of DNTT taken by an AMF in the case of using Compound 3 as a Janus-type triptycene derivative, and FIG. 6 is an image of DNTT taken by an AMF in the case of using Compound 4 of the present invention as a Janus-type triptycene derivative.

As is apparent from these results, the crystal of DNTT is larger in the case of providing a Janus-type triptycene derivative layer (see FIG. 5 and FIG. 6) as compared to the case of Parylene alone (see FIG. 4). Moreover, the crystal of DNTT is even larger in the case of using Compound 4 of the present invention (see FIG. 6) although Janus-type triptycene derivatives are used in the same manner. It is known that the size of grain diameter of crystal DNTT greatly affects the properties of a device which made from the DNTT, and as a result, it is considered that the improvement in properties of a device is achieved by using the Janus-type triptycene derivative of the present invention (see Examples to be described later).

As described above, the Janus-type triptycene derivative of the present invention which is represented by Formula [I] and of which the steric hindrance is eliminated not only exhibits excellent regularity of film but also has excellent nature in improving the properties of a semiconductor.

With regard to the method for producing the Janus-type triptycene derivatives represented by Formula [I] of the present invention, the Janus-type triptycene derivatives can be produced by partially substituting 1,8,13-trimethoxytriptycene which first has been successfully separated and purified by the present inventors or a derivative thereof as a key intermediate.

The compound represented by Formula [I] of the present invention can be produced, for example, as follows. Only one or two of the hydroxy groups of 1,8,13-trihydroxytriptycene that is one of the derivatives of 1,8,13-trimethoxytriptycene are alkylate by using an alkylating agent such as a methylating agent or an ethylating agent to produce 1-alkoxy-8,13-dihydroxytriptycene or 1,8-dialkoxy-13-hydroxytriptycene. Subsequently, the resulting product is reacted with a compound represented by the following Formula [II], $$Y^1-R^1-Z \qquad [II]$$

(in Formula [II], $R^1$ and Z represent the groups described above, and $Y^1$ represents a leaving group such as a halogen). Alternatively, it may be produced by first reacting 1,8,13-trihydroxytriptycene with the compound represented by Formula [II] described above and subsequently reacting the resultant with an alkylating agent. These reactions are basically a substitution reaction and can be conducted in conformity to various kinds of known substitution reactions.

In addition, in a case in which the substituent Z is reactive, it is possible to conduct the substitution reaction after protecting Z with various kinds of protecting groups, or to conduct the substitution reaction using a compound having a precursor of Z. For example, in a case in which the substituent Z is a carboxyl group, a compound having a cyano group is used as a precursor and after the substitution reaction the precursor is hydrolyzed to obtain a compound having a substituent Z. In a case in which Z is an ester group, the substitution reaction may be conducted without protecting Z, or the substitution reaction and the hydrolysis may be conducted to obtain a compound having a carboxyl group and then the carboxyl group is esterified. Although the protective group and the deprotection are well known to those skilled in the art, see Protective Group in Organic Synthesis (John Wiley and Sons, 1991) written by T. W. Green, if necessary.

In addition, a compound in which the substituent of the triptycene is a carbonyl group such as a formyl group makes it possible to produce a compound of Formula [I] in which the group X is —C≡C— by using the Wittig reagent.

For example, it is also possible to produce compound having the ester group as an end group described above by reacting 1,8,13-trihydroxytriptycene as a raw material with methyl 12-bromododecanoate (it may be chloro, iodo, or a pseudohalide such as a tosylate ester instead of bromo) by the Williamson synthesis reaction in the presence of a base.

It is possible to use a solvent in these reactions if necessary. Examples of such a solvent may include a ketone-based solvent such as acetone or methyl ethyl ketone, an ether-based solvent such as diethyl ether or THF, an aprotic polar solvent such as DMF, DMA, or DMSO, an alcohol-based solvent such as ethanol, an aromatic hydrocarbon-based solvent such as toluene or xylene, and a halogen-based solvent such as dichloromethane or chlorobenzene, but the solvent is not limited thereto. In addition, it is also possible to conduct the reaction in the presence of various kinds of reagents if necessary. A base is preferred as such a reagent, and examples of the base may include an alkali metal carbonate such as potassium carbonate, sodium carbonate or cesium carbonate, and an alkali metal hydroxide such as sodium hydroxide or potassium hydroxide, but the base is not limited thereto. It is also possible to use an organic base such as a trialkylamine as the base, but an inorganic base is preferred.

The reaction temperature can be arbitrarily set as long as the reaction properly proceeds, but the temperature is usually preferably in the range of from room temperature to the boiling point of the solvent.

In order to adjust the number of introduced substituents to one or two, the number can be adjusted by controlling the number of moles of the reagent, shortening the reaction time, adjusting the reaction temperature, increasing the amount of the solvent, or combining these.

As the method to isolate the intended product from the reaction mixture and to purify it, a usual isolation and purification means, for example, a method such as solvent extraction, recrystallization, reprecipitation, silica gel column chromatography, or gel filtration chromatography can be conducted. In addition, in a case in which the product is optically active, the optical resolution thereof can also be conducted if necessary.

The compound represented by Formula [I] of the present invention can be produced by further conducting the substitution reaction of the compound into which one or two substituents are introduced as described above by using a reagent represented by the following Formula [III] and the same method described above $$Y^1-R^2 \qquad [III]$$

(in Formula [III], $R^2$ represents the group described above and $Y^1$ represents a leaving group such as a halogen) if necessary.

In the Janus-type triptycene derivative represented by Formula [I] of the present invention, the benzene rings arranged in a three-blade shape of triptycenes integrate in a nest shape, and it is thus possible to reasonably construct a two-dimensional molecular assembly with controlled dimensionality and to form a film by utilizing such a characteristic integration behavior. Furthermore, the steric hindrance of the Janus-type triptycene derivative represented by Formula [I] of the present invention itself is eliminated, and it is thus possible to form a film exhibiting superior regularity. As the method for producing the film of the present invention, it is possible to arbitrarily select a spin coating method, a dipping method, a casting method, an ink jet method, an ultrasonic method, a vapor phase method, a vapor deposition method or the like, but a spin coating method, a dipping method, a casting method, an ink jet method, a vapor deposition method or the like is preferred since the compound of the present invention can be dissolved in an organic solvent.

The spin coating method forms a thin film having a uniform film thickness by dropping a solution on a rotating substrate at a high speed. The dipping method forms a film by immersing a substrate in a solution. The casting method (including drop casting) forms a film by dropping a solution on a substrate and then drying the substrate to remove the solvent, but the film thickness is not always uniform. The ink jet method forms a film by dropping a trace amount of solution at an arbitrary position. The film of the present invention may be produced by any of these known film-forming methods, but it may also be produced by a method of forming a film at a liquid/liquid interface since the film of the present invention exhibits a unique integration behavior. For example, it is possible to bring a solution prepared by dissolving the compounds of the present invention in an organic solvent which does not dissolve in water into contact with water to form an interface of water/organic solvent and to produce a film at the interface.

In addition, some of the compounds among the compounds represented by Formula [I] of the present invention can form a film by a vapor deposition method and preferably a vacuum deposition method. In particular, a compound which has a relatively low melting point and a high decomposition temperature is preferred. The vapor deposition method in the present invention can be conducted by a usual vapor deposition method. For example, it is preferable that the compound is evaporated by heating to the melting point or higher of the compound or the compound is sublimated in a case in which the compound is sublimable, and then the vapor deposition is conducted under the reduced pressure of from $10^{-5}$ Pa to $10^{-3}$ Pa. The temperature of the substrate may be near room temperature, but it is preferably about from 50° C. to 100° C. Examples of the compound of the present invention that is suitable for forming a film by a vapor deposition method may include compounds of Formula [I] in which X is —CH$_2$—, Z is a hydrogen atom, $R^1$ is an alkylene group having from 8 to 15 carbon atoms and preferably an alkylene group having from 9 to 12 carbon atoms.

The Janus-type triptycene derivative of the present invention that is represented by Formula [I] and used in the formation of the film can be used as a compound purified as a single compound, but two kinds or three or more kinds of the Janus-type triptycene derivatives represented by Formula [I] of the present invention can also be used by being mixed together. Furthermore, it is also possible to use a mixture with the Janus-type triptycene derivative which has been previously reported (see Patent Document 16) and of which three substituents are the same group.

This means that it is not necessarily required to purify and separate only a single substituted form, for example, a disubstituted form from the substituted forms generated by the first substitution reaction of 1,8,13-trimethoxytriptycene or a derivative thereof. The substituted forms generated by the first substitution reaction of 1,8,13-trimethoxytriptycene or a derivative thereof is a mixture of an unsubstituted form, a monosubstituted form, a disubstituted form, and a trisubstituted form in some cases, but the mixture can be used as it is even if the mixture is such a mixture as long as the properties of the film that has been described in the present specification can be maintained. It is not required to purify the mixture always into a single compound to use.

In a case in which the amount of the trisubstituted form exceeds, for example, 60% and preferably 80% in the mixture, it is not possible to eliminate the steric hindrance due to the substituents in a formed film. As a result, it is not possible to maintain the properties of the film that has been described in the present specification. In such a case, it departs from the scope of the present invention. However, in a case in which the amount of the trisubstituted form is small and the steric hindrance is thus sufficiently eliminated, a formed film can maintain the properties of the film that has been described and therefore the case falls within the scope of the present invention.

It is possible to use the solid substrate that is described above when producing the film of the present invention on a solid substrate. Furthermore, it is also possible to adopt as the solid substrate: a solid substrate prepared by subjecting the solid substrates to a cleaning treatment by ultraviolet light (UV), ozone, or the like; and a layered body prepared by layering a connecting terminal such as an electrical wire or an electrode or another layer such as an insulating layer or a conductive layer on the solid substrates. As the solid substrate to be used in the present invention, a glass substrate or an organic substrate is preferred and in particular a substrate subjected to a cleaning treatment is preferred among these.

Examples of the method of producing the film of the present invention on a solid substrate may include a method including a process of preparing a solution by dissolving the Janus-type triptycene derivatives represented by Formula [I] of the present invention in an organic solvent, subsequently, a process of coating or spin coating the solution on a solid substrate or immersing the solid substrate in the solution, and a process of drying the solid substrate to remove the solution.

In addition, examples of the method of producing the film of the present invention at an interface may include a method including a process of preparing a solution by dissolving the Janus-type triptycene derivatives represented by Formula [I] of the present invention in an organic solvent which is non-miscible with a second solvent such as water, subsequently, a process of forming an interface by adding the second solvent such as water to the solution and forming a film at the interface, a process of separating the film thus produced, and a process of drying the film thus separated.

The film thickness of the film of the present invention produced by such a method is not particularly limited, but the average thickness in the case of a monolayer is from 0.1 nm to 5 nm and preferably from 1 nm to 3 nm. In addition, the average thickness in the case of a multilayer film is from 2 nm to 50 nm and preferably from 3 nm to 30 nm. Furthermore, it is possible to produce a film having a great film thickness in the case of producing a film at a liquid/liquid interface, and it is also possible to have a film thickness of from 30 nm to 1000 nm and preferably from 50 nm to 500 nm.

The organic solvent used when producing the film is not particularly limited as long as it can dissolve the Janus-type triptycene derivative represented by Formula [I] of the present invention, and examples thereof may include a lactone such as γ-butyrolactone; a ketone such as acetone, methyl ethyl ketone, cyclohexanone, methyl-n-amyl ketone, methyl isoamyl ketone, or 2-heptanone; a monohydric alcohol such as methanol, ethanol, or isopropanol; a polyhydric alcohol such as ethylene glycol, diethylene glycol, propylene glycol, or dipropylene glycol, and any derivatives thereof; a glycol ester such as ethylene glycol monoacetate, diethylene glycol monoacetate, propylene glycol monoacetate, or dipropylene glycol monoacetate; a mono ether such as monomethyl ether, monoethyl ether, monopropyl ether, monobutyl ether of the polyhydric alcohol or the ester or a mono ether ester; an ester such as methyl lactate, ethyl lactate (EL), methyl acetate, ethyl acetate, butyl acetate, methyl pyruvate, ethyl pyruvate, methyl methoxypropionate, or ethyl ethoxypropionate; an aromatic organic solvent such as anisole, ethyl benzyl ether, cresyl methyl ether, diphenyl ether, dibenzyl ether, phenetole, butylphenyl ether, ethylbenzene, diethylbenzene, amylbenzene, isopropylbenzene, toluene, xylene, cymene, or mesitylene; a cyclic ether such as dioxane or THF; an amide such as dimethylformamide (DMF) or dimethylacetamide (DMA); and a sulfur-containing solvent such as dimethyl sulfoxide (DMSO). These organic solvents may be used singly or as a mixed solvent of two or more kinds thereof.

Preferred examples of the organic solvent may include an amide such as dimethylformamide (DMF) or dimethylacetamide (DMA), a cyclic ether such as dioxane or THF, and a sulfur-containing solvent such as dimethyl sulfoxide (DMSO). Particularly preferred examples of the solvent may include a polar solvent such as dimethylformamide (DMF) or tetrahydrofuran (THF).

The amount of the organic solvent used is not particularly limited, and the amount may be appropriately set in consideration of the thickness of the film to be produced and the conditions for production. The concentration of the Janus-type triptycene derivative represented by Formula [I] of the present invention in 100 mL of an organic solvent is preferably from 0.01 mg to 1000 mg, more preferably from 0.1 mg to 100 mg, and still more preferably from 0.1 mg to 10 mg.

As the temperature when producing the film of the present invention, the production can be usually performed at room temperature but can also be performed under heating or cooling depending on the kind of the solvent or the conditions for production.

As the drying in the production of the film of the present invention, natural drying is sufficient, but the film can also be dried by a method of blowing dry air, nitrogen or the like or by heating if necessary.

In addition, after formation of the film, cleaning of the film thus produced may be conducted using an organic solvent such as methanol or chloroform or purified water, but it is not particularly required to clean the film.

In the case of producing the film of the present invention at an interface, the film produced at the interface can be separated by transferring the film to a substrate such as a glass substrate. The film thus separated can be dried by the method described above.

The film of the present invention produced in this manner can be further subjected to an annealing treatment, but the annealing treatment can be omitted since the film of the present invention exhibits excellent regularity. In the case of conducting the annealing treatment, the annealing treatment for the film that is produced by a spin coating method, a dipping method, a casting method, an ink jet method or the like is conducted by heating the film at approximately the same temperature as the melting point of the Janus-type triptycene derivative represented by Formula [I] of the present invention, preferably about from 100° C. to 230° C., more preferably about from 130° C. to 230° C., and even more preferably about from 150° C. to 200° C.

In addition, the annealing treatment for the film that is produced by a vapor deposition method is conducted by heating at about from 100° C. to 200° C. and preferably about from 110° C. to 150° C.

The annealing treatment can be usually conducted in the air, but it may be conducted in an inert gas stream such as a nitrogen stream. The annealing time is not particularly limited, but it is sufficient to conduct the annealing treatment for usually from 5 minutes to 50 minutes and preferably about from 10 minutes to 30 minutes.

The film of the present invention can be formed to have a single-layer structure or a bilayer structure in which the end groups Z face each other between the molecules depending on the kind of the end group Z in Formula [I]. In addition, it is possible to adjust the thickness of the film by the production method. Therefore, it is possible to provide a thin film that is suitable for a wide range of applications as an electronic material, an optical material, a surface treatment material and the like or a structure that is suitable for a wide range of applications as a structure integrated with a solid substrate.

The electronic device of the present invention can be manufactured in accordance with a method of manufacturing an electronic device of the related art. At that time, the electronic device of the present invention can be manufactured using the organic thin film of the present invention that has been described above instead of an organic thin film, in particular, a SAM of the related art. As is described above, the organic thin film of the present invention is not dependent on the substrate, and thus it is possible to form an intended organic thin film on various kinds of organic or inorganic substrates by the method described above.

The production example of a thin film transistor may include a method to be described below.

Aluminum is deposited on a silicon wafer, patterned, and subsequently incinerated in an oxygen plasma to obtain a surface of aluminum oxide, and then an $Al_2O_3/Al$ gate electrode having an insulating layer of aluminum oxide is patterned. A solution of the Janus-type triptycene derivatives represented by Formula [I] of the present invention is drop-casted thereon and the wafer is dried. The annealing treatment may be conducted at about 200° C. if necessary. An organic thin film containing the Janus-type triptycene derivatives represented by Formula [I] of the present invention is formed on the patterned $Al_2O_3/Al$ gate electrode in this manner. Subsequently, an organic semiconductor such as DNTT (dinaphthothienothiophene) is deposited on the organic thin film and the $Al_2O_3/Al$ gate electrode to form an organic semiconductor layer. Thereafter, gold is deposited on the organic semiconductor layer by a vacuum deposition method to form a source electrode and a drain electrode.

In the above method, it is also possible to form a capacitor by directly depositing gold on the organic thin film without forming an organic semiconductor layer.

The capacitor of the present invention is characterized by having a dielectric layer consisting of the organic thin film of the present invention that has been described above between the electrodes. The capacitor of the present invention can also further contain a second dielectric in the dielectric layer. The second dielectric is not particularly limited as long as it is a dielectric used in a capacitor, but an organic dielectric is preferred. In addition, the dielectric layer preferably has a layered structure in the case of containing a second dielectric.

In addition, in the case of manufacturing an electronic paper, first a transparent and flexible polymer substrate such as a polycarbonate substrate is cleaned, and subsequently a pattern is formed on the substrate using an organic conductive material such as PEDOT (polyethylenedioxythiophene) or metal fine particles such as copper to form a gate electrode. Next, a layer of an organic insulator such as a polyimide, poly(methyl methacrylate), or poly(p-xylylene) is formed on a part or the entire surface of the substrate. Then, an organic thin film containing the Janus-type triptycene derivatives represented by Formula [I] of the present invention is formed so as to overlap with the gate electrode. Furthermore, an organic semiconductor such as DNTT (dinaphthothienothiophene) is deposited thereon to form an organic semiconductor layer. Thereafter, gold is deposited on the organic semiconductor layer by a vacuum deposition method or the like to form a source electrode and a drain electrode.

Examples of the insulator in these thin film transistors may include various insulators such as an inorganic material, an organic material, or an organic low-molecular amorphous material. Examples of the inorganic material may include a single-metal oxide such as $SiO_2$, $Al_2O_3$, $Ta_2O_5$, or $ZrO_2$, a composite oxide such as strontium titanate or barium strontium titanate, a nitride such as SiNx, an oxynitride, or a fluoride. Examples of the organic material may include polyimide, poly(methyl methacrylate), poly(p-xylylene), polyvinyl phenol, poly(methyl methacrylate), polystyrene, benzocyclobutene, cyanoethyl pullulan, polyvinylidene fluoride, a vinylidene-tetrafluoroethylene copolymer, and other polymer materials. Examples of the organic low-molecular amorphous material may include cholic acid and methyl cholate.

As the method of forming these insulators, it is possible to adopt various film forming methods such as vapor deposition, sputtering, plasma CVD (Chemical Vapor Deposition), anodic oxidation of the gate electrode, coating, and attachment from a solution depending on the material of the insulator. The thickness of the gate insulating layer can be from about 10 nm to about 500 nm although it also depends on the material.

Examples of the semiconductor in these thin film transistors may include an organic semiconductor material or an inorganic oxide semiconductor material. As the organic semiconductor material, it is possible to use a polymer organic semiconductor material such as a polythiophene, polyallylamine, a fluorine-bithiophene copolymer, poly(thienylene vinylene), poly(alkyl thiophene), and any derivative thereof; a low molecular organic semiconductor material such as DNTT (dinaphthothienothiophene), oligothiophene, pentacene, tetracene, copper phthalocyanine, perylene, and any derivative thereof. In addition, it is also possible to use a carbon compound such as carbon nanotubes or a fullerene, a semiconductor nanoparticle dispersion or the like as a material for the semiconductor layer. These organic semiconductor materials can be used as an ink-like solution or a dispersion by being dissolved or dispersed in an aromatic solvent such as toluene. In addition, these organic semiconductor materials can also be formed into a film by a vapor deposition method. Examples of the oxide semiconductor material may include an oxide containing one or more kinds of elements among zinc, indium, tin, tungsten, magnesium, and gallium. Examples of the oxide semiconductor material may include known materials such as zinc oxide, indium oxide, indium zinc oxide, tin oxide, tungsten oxide, and indium gallium zinc oxide (In—Ga—Zn—O), but the oxide semiconductor material is not limited to these materials. The structure of these materials may be any of a monocrystalline structure, a polycrystalline structure, a microcrystalline structure, a mixed crystalline structure of crystalline/amorphous, a structure having a nanocrystal interspersed within an amorphous matrix, and an amorphous structure.

Examples of the substrate in these thin film transistors may include a flexible plastic material such as polyethylene terephthalate (PET), polyimide, polyether sulfone (PES), polyethylene naphthalate (PEN), poly(methyl methacrylate), or polycarbonate; a glass substrate such as quartz; a silicon wafer; and an aluminum wafer.

In addition, the thin film transistor can be provided with a sealing layer and a light shielding layer if necessary. It is possible to select and use a material from the same materials as the materials for the insulator as the material for the sealing layer, and to use those which are prepared by dispersing a light shielding material such as carbon black in a gate material as the light shielding layer.

As apparent from the examples described above, the organic thin film of the present invention can be a component of an electronic device, and this makes it possible to obtain an electron device excellent in stability. In other words, the present invention provides an electronic device material including an organic thin film containing the Janus-type triptycene derivatives represented by Formula [I] of the present invention.

In addition, it is provided a method of manufacturing the electronic device of the present invention which is characterized by providing an organic thin film containing the Janus-type triptycene derivatives represented by Formula [I] of the present invention in an electronic device.

It is possible to form an electronic circuit depending on the purpose such as amplification or data processing by combining appropriately the electronic devices or electronic elements of the present invention manufactured as described above and by wiring them on a substrate by a usual method. The electronic circuit formed on a substrate in this manner is a circuit board of the present invention. The circuit board of the present invention may be one sheet or may be formed as plural sheets of two or more depending on the purpose.

Furthermore, it is possible to manufacture the electronic apparatus of the present invention by appropriately combining such circuit boards. The electronic apparatus of the present invention itself may be various kinds of electronic products or may be a device forming a part of the electronic product, for example, a device such as a display device.

Hereinafter, the present invention will be described in more detail with reference to Examples and Production Examples, but the present invention is not limited by these Examples and Production Examples in any way.

Production Example 1

Production of Trimethoxytriptycene Mixture
Trimethoxytriptycene was produced in accordance with the following reaction formula.

[Chemical Formula 5]

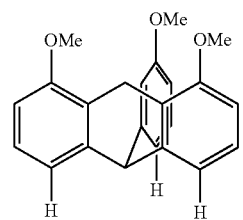

5a

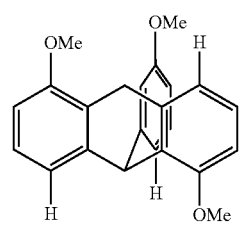

5b

A suspension was prepared by adding acetonitrile (750 mL) to 1,8-dimethoxyanthracene (22.3 g, 93.7 mmol) and cesium fluoride (CsF) (85.3 mg, 561.0 mmol) and heated to 80° C. To this suspension, 2-methoxy-6-trimethylsilyloxytrifluoromethylsulfonate (61.5 g, 188 mmol) was added dropwise, and the mixture was refluxed while heating for 5 hours. Acetonitrile was distilled off from the reaction mixture thus obtained under reduced pressure, the residue was washed with water and then washed with a mixed solvent of hexane/chloroform (1/1, v/v), thereby obtaining intended trimethoxytriptycene (yield: 22.2 g, 64.5%). The trimethoxytriptycene thus obtained was revealed to be a mixture of 1,8,13-trimethoxytriptycene (Compound 5a) and 1,8,16-trimethoxytriptycene (Compound 5b) of 2:1 by the NMR measurement.

Compound 5a:
$^1$H-NMR (400 MHz, CDCl$_3$): δ (ppm) 7.01 (d, J=0.7 Hz, 3H), 6.90 (dd, J=7.3, 1.0 Hz, 3H), 6.80 (s, 1H), 6.58 (dd, J=8.2, 0.7 Hz, 3H), 5.38 (s, 1H), 3.86 (s, 9H).

Compound 5b:
$^1$H-NMR (400 MHz, CDCl$_3$): δ (ppm) 7.09-7.07 (d, J=7.2 Hz, 1H), 7.06-7.04 (d, J=7.2 Hz, 2H), 6.93-6.89 (t, J=7.8 Hz, 1H), 6.93-6.89 (t, J=7.7 Hz, 2H), 6.58-6.56 (d, J=7.7 Hz, 2H), 6.56-6.54 (d, J=7.8 Hz, 2H), 6.35 (s, 1H), 5.87 (s, 1H), 3.84 (s, 6H), 3.83 (s, 3H).

Production Example 2

Production of 1,8,13-trimethoxytriptycene (Compound 5a) single crystal

[Chemical Formula 6]

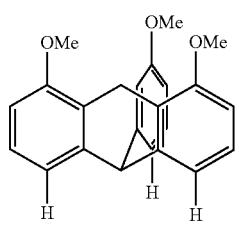

5a

The trimethoxytriptycene mixture (10.0 mg) produced in Production Example 1 was crystallized by dissolving in chloroform and allowing to stand, thereby obtaining 1,8,13-trimethoxytriptycene (2.0 mg) of the title.

The crystal thus obtained was subjected to the single-crystal X-ray structural analysis, and the result was as follows. This crystal had an orthorhombic crystal system, and the values of a, b, and c of unit cell were 15.608, 13.388, and 8.041, respectively in a unit of angstrom. The value of V was 1680 cubic angstrom.

The structure of the crystal thus obtained is illustrated in FIG. 3 as a schematic view.

Production Example 3

Production of 1,8,13-trihydroxytriptycene (Compound 6)

[Chemical Formula 7]

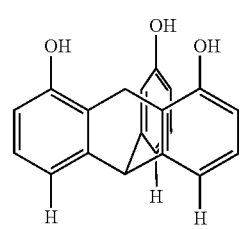

6

To the trimethoxytriptycene mixture (22.0 g, 62.9 mmol) produced in Production Example 1, 320 mL of dichloromethane was added to prepare a suspension, and boron tribromide ($BBr_3$) (18.2 mL, 192 mmol) was added to this, and the mixture was stirred for 4 hours at 0° C. To the reaction mixture, 200 mL of water was added, and the powder thus precipitated was collected by filtration and dried under reduced pressure. The powder thus obtained was dissolved in 80 mL of dimethylformamide, the mixture was allowed to stand at 500, and as a result, a colorless crystal was precipitated. This crystal was collected by filtration and washed with chloroform, thereby selectively obtaining 1,8,13-trihydroxytriptycene (Compound 6) (yield: 9.14 g, 71%) of the title.

Compound 6:
$^1$H-NMR (400 MHz, acetone-$d_6$): δ (ppm) 8.35 (br, s, 3H), 6.94-6.93 (d, J=7.2 Hz, 3H), 6.86 (s, 1H), 6.79-6.75 (dd, J=7.2, 0.9 Hz, 3H), 6.56-6.54 (dd, J=8.1, 0.9 Hz, 3H), 5.44 (s, 1H).

Production Example 4

Production of 1,8,13-trihydroxy-4,5,16-tribromo-triptycene (Compound 7)

[Chemical Formula 8]

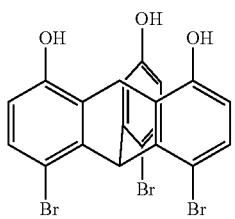

7

Compound 6 (1.10 g, 3.64 mmol) obtained in Production Example 3 and p-toluenesulfonic acid monohydrate (0.692 g, 3.64 mmol) were dissolved in 72 mL of DMF, N-bromosuccinimide (1.94 mg, 10.9 mmol) was added to this while being cooled with ice, and the mixture was stirred for 4 hours while being cooled with ice. To the reaction mixture, 200 mL of a 10% aqueous solution of sodium thiosulfate was added and the extraction operation was conducted with diethyl ether. The diethyl ether solution thus obtained was dried over sodium sulfate and filtered, and diethyl ether was then distilled off under reduced pressure. The residue was subjected to silica gel column chromatography using a mixed solvent of chloroform/methanol (9/1, v/v) as a solvent, thereby obtaining 1,8,13-trihydroxy-4,5,16-tribromo-triptycene (Compound 7) (yield: 1.20 g, 61%) of the title.

Compound 7:
$^1$H-NMR (400 MHz, $CDCl_3$): δ (ppm) 7.08-7.06 (d, J=8.7 Hz, 3H), 6.96 (s, 1H), 6.82 (s, 1H), 6.63-6.61 (d, J=8.7 Hz, 3H).

Production Example 5

Production of 1,8,13-tris(tert-butyldimethylsilyloxy)-4,5,16-tribromotriptycene (Compound 8)

[Chemical Formula 9]

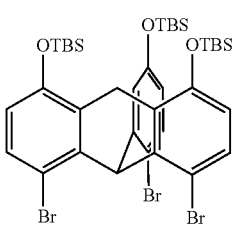

8

A solution of Compound 7 (4.65 g, 8.63 mmol) produced in Production Example 4, imidazole (2.38 g, 34.9 mmol), and tert-butyldimethylchlorosilane (5.26 g, 34.9 mmol) in 50 mL of dimethylformamide was stirred for 12 hours at 60° C. To the reaction mixture, 200 mL of diethyl ether was added, the mixture was washed with water, and the organic layer was dried over sodium sulfate, filtered, and then subjected to distillation under reduced pressure. The residue was recrystallized from 100 mL of hexane, thereby obtaining 1,8,13-tris(tert-butyldimethylsilyloxy)-4,5,16-tribromotriptycene (Compound 8) (Yield: 4.20 g, 55%) of the title.

Compound 8:

$^1$H-NMR (400 MHz, CDCl$_3$): δ (ppm) 7.04 (d, J=8.4 Hz, 3H), 6.83 (s, 1H), 6.55 (s, 1H), 6.46 (d, J=8.4 Hz, 3H), 0.97 (s, 27H), 0.25 (s, 18H).

Production Example 6

Production of 1,8,13-tris(tert-butyldimethylsilyloxy)-4,5,16-triformyltriptycene (Compound 9)

[Chemical Formula 10]

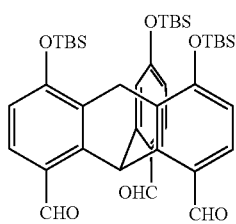

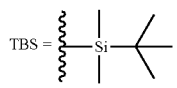

9

Compound 8 (4.20 g, 4.76 mmol) produced in Production Example 5 was dissolved in 50 mL of diethyl ether and a solution of n-BuLi pentane (concentration: 1.54 M, 21.6 mL) was added to this dropwise little by little at −78° C. After the dropwise addition was completed, the mixture was further stirred at this temperature for 30 minutes, and 37 mL of DMF was then added to this dropwise. The reaction temperature was returned to room temperature, 100 mL of diethyl ether was added to the reaction mixture, and the mixture was washed with water, and the organic layer was dried over sodium sulfate, filtered, and subjected to distillation under reduced pressure. The residue was subjected to silica gel column chromatography using a mixed solvent of chloroform/methanol (98/2, v/v) as a solvent, thereby obtaining 1,8,13-tris(tert-butyldimethylsilyloxy)-4,5,16-triformyltriptycene (Compound 9) (yield: 2.88 g, 83%) of the title.

Compound 9:

$^1$H-NMR (400 MHz, CDCl$_3$): δ (ppm) 10.4 (s, 3H), 9.28 (s, 1H), 7.44 (d, J=8.6 Hz, 3H), 6.75 (s, 1H), 6.71 (d, J=8.6 Hz, 3H), 0.99 (s, 27H), 0.34 (s, 18H).

Production Example 7

Production of 1,8,13-tris(tert-butyldimethylsilyloxy)-4,5,16-tris(2,2-dibromovinyl)-triptycene (Compound 10)

[Chemical Formula 11]

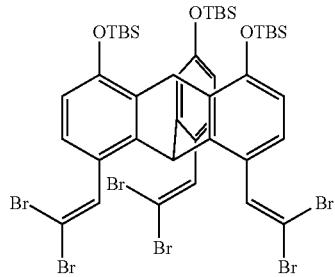

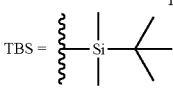

10

Compound 9 (2.88 g, 3.95 mmol) produced in Production Example 6 and carbon tetrabromide (CBr$_4$) (5.90 g, 17.8 mmol) were dissolved in 15 mL of dichloromethane (DCM), and a DCM solution (25 mL) of triphenylphosphine (PPh$_3$) (9.31 g, 35.5 mmol) was gradually added thereto dropwise while being cooled with ice. The reaction mixture was stirred for 3 hours while being cooled with ice. The reaction mixture was filtered, and the filtrate was distilled off under reduced pressure to dry the mixture. The residue was subjected to silica gel column chromatography using a mixed solvent of chloroform/hexane (1/4, v/v) as a solvent, thereby obtaining 1,8,13-tris(tert-butyldimethylsilyloxy)-4,5,16-tris(2,2-dibromovinyl)-triptycene (Compound 10) (yield: 2.97 g, 63%) of the title.

Compound 10:

$^1$H-NMR (400 MHz, CDCl$_3$): δ (ppm) 7.26 (s, 1H), 6.99 (d, J=8.7 Hz, 3H), 6.60 (s, 1H), 6.56 (d, J=8.7 Hz, 3H), 5.70 (s, 1H), 1.01 (s, 27H), 0.30 (s, 18H).

Production Example 8

Production of 1,8,13-tris(tert-butyldimethylsilyloxy)-4,5,16-triethynyltriptycene (Compound 11)

[Chemical Formula 12]

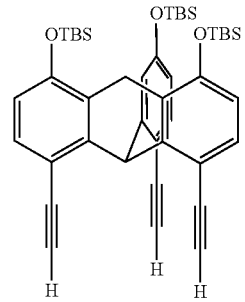

11

-continued

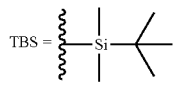

Compound 10 (2.97 g, 2.48 mmol) produced in Production Example 7 was dissolved in 60 mL of THF, and a solution of n-BuLi pentane (concentration: 1.64 M, 15.1 mL) was added to this dropwise little by little at −78° C. After the dropwise addition was completed, the mixture was further stirred for 30 minutes at this temperature, the temperature was then returned to room temperature, and 50 mL of water was added to the reaction mixture. To the reaction mixture, 100 mL of diethyl ether was added, the mixture was washed with water, and the organic layer was dried over sodium sulfate, filtered, and subjected to distillation under reduced pressure. The residue was subjected to silica gel column chromatography using a mixed solvent of chloroform/hexane (1/4, v/v) as a solvent, thereby obtaining 1,8,13-tris(tert-butyldimethylsilyloxy)-4,5,16-triethynyltriptycene (Compound 11) (yield: 1.72 g, 97%) of the title.

Compound 11:
$^1$H-NMR (400 MHz, CDCl$_3$): δ (ppm) 7.10 (s, 1H), 7.02 (d, J=8.7 Hz, 3H), 6.54 (s, 1H), 6.50 (d, J=8.7 Hz, 3H), 3.26 (s, 3H), 0.97 (s, 27H), 0.25 (s, 18H).

Production Example 9

Production of 1,8,13-tri(trifluoromethylsulfonyloxy)triptycene (Compound 12)

[Chemical Formula 13]

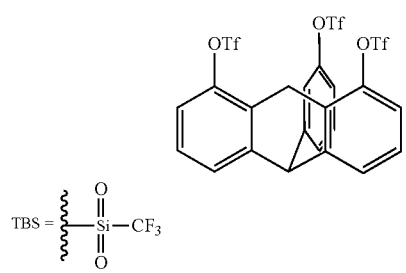

Compound 6 (300 mg, 0.992 mmol) produced in Production Example 3 was dissolved in 0.80 mL of pyridine and 15 mL of dichloroethane, trifluoromethanesulfonic anhydride (Tf$_2$O) (1.68 g, 5.95 mmol) was added to this, and the mixture was stirred for 3 hours at 60° C. The reaction mixture was washed with water by a separating operation, and the organic layer was dried over sodium sulfate, filtered, and dried through distillation under reduced pressure. The residue was dissolved in 30 mL of hexane and allowed to stand at 5° C., thereby obtaining 1,8,13-tri(trifluoromethylsulfonyloxy)triptycene (Compound 12) as a colorless transparent crystal (yield: 575 mg, 83%) of the title.

Compound 12:
$^1$H-NMR (400 MHz, acetone-d$_6$): δ (ppm) 7.77 (d, J=7.4 Hz, 3H), 7.39 (t, J=8.1 Hz, 3H), 7.27 (d, J=8.6 Hz, 3H), 6.58 (s, 1H), 6.31 (s, 1H).

Production Example 10

Production of 1,8,13-tricyanotriptycene (Compound 13)

[Chemical Formula 14]

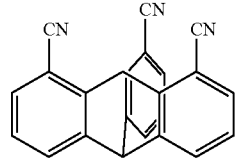

Compound 12 (200 mg, 0.29 mmol) produced in Production Example 9 was dissolved in 3.0 mL of DMF, and 1,1'-bis(diphenylphosphino) ferrocene (ddpf) (100 mg, 0.18 mmol) and dba palladium (Pd$_2$dba$_3$) (165 mg, 0.18 mmol) were added to this, and the mixture was stirred for 1 hour at 90° C., zinc cyanide (ZnCN$_2$) (336 mg, 2.86 mmol) was then added to this, and the reaction thereof was conducted for 12 hours at 90° C. To the reaction mixture, 5.0 mL of water and 3.0 mL of a 26% ammonia aqueous solution were added, and the precipitate thus precipitated was collected through filtration, further washed with 3.0 mL of a 26% ammonia aqueous solution and 10.0 mL of water, and dried under reduced pressure. The residue was subjected to Soxhlet extraction with acetone, and the acetone was distilled off, thereby obtaining 1,8,13-tricyanotriptycene (Compound 13) (yield: 85.8 mg, 91%) of the title.

Compound 13:
$^1$H-NMR (400 MHz, acetone-d$_6$): δ (ppm) 7.95 (d, J=7.3 Hz, 3H), 7.60 (d, J=8.6 Hz, 3H), 7.40 (t, J=8.1 Hz, 3H), 6.77 (s, 1H), 6.26 (s, 1H).

Production Example 11

Production of Compound 1 to be presented below

[Chemical Formula 15]

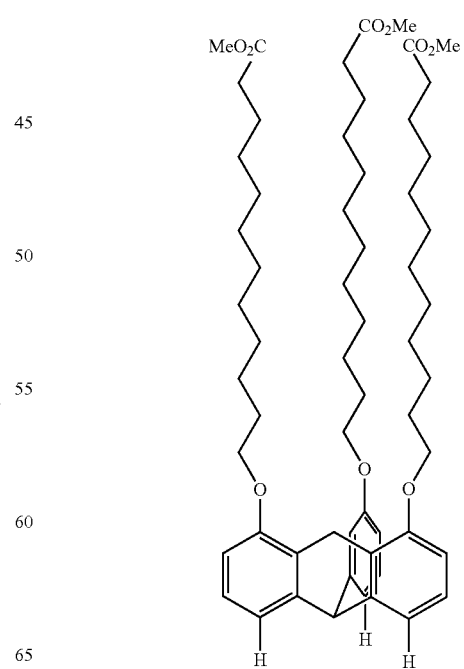

Compound 6 (102 mg, 0.337 mmol) produced in Production Example 3 was dissolved in 10.0 mL of dimethylformamide, potassium carbonate (190 mg, 1.34 mmol) and methyl 12-bromododecanoate (373 mg, 1.21 mmol) were added thereto, and the mixture was stirred for 10 hours at 70° C. To the reaction mixture, 50 mL of diethyl ether was added, the mixture was washed with water, and the organic layer was dried over magnesium sulfate, filtered, and distilled off under reduced pressure. The residue was subjected to the gel filtration chromatography using chloroform as a solvent, thereby obtaining Compound 1 (yield: 261 g, 82%) of the title.

Compound 1:

$^1$H-NMR (400 MHz, CDCl$_3$): δ (ppm) 6.99 (d, J=7.3 Hz, 3H), 6.89-6.84 (m, 4H), 6.54 (d, J=8.3 Hz, 3H), 5.37 (s, 1H), 3.96 (t, J=6.6 Hz, 6H), 3.67 (s, 9H), 1.85 (m, 6H), 1.705-1.270 (m, 60H).

Production Example 12

Production of Compound 2 to be Presented Below

[Chemical Formula 16]

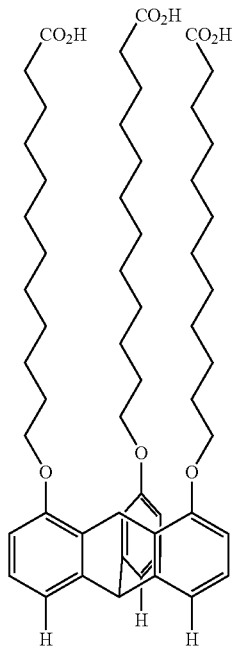

Compound 1 (140 mg, 0.150 mmol) produced in Production Example 11 was dissolved in 5.0 mL of tetrahydrofuran, potassium hydroxide (84.0 mg, 1.50 mmol) was added thereto, and the mixture was refluxed while heating for 12 hours. The reaction mixture was cooled to room temperature, hydrochloric acid (1.0 M, 10 mL) was added thereto, and the mixture was stirred for 10 minutes. The white powder thus precipitated was collected through filtration, washed with water, and dried, thereby obtaining Compound 2 (yield: 30.0 mg, 23%) of the title.

Compound 2

$^1$H-NMR (400 MHz, DMSO-d$_6$): δ (ppm) 11.95 (s, 3H), 7.02 (d, J=7.6 Hz, 3H), 6.89 (t, J=7.6 Hz, 3H), 6.67 (s, 1H), 6.63 (d, J=7.6 Hz, 3H), 5.53 (s, 1H), 3.92 (t, J=6.4 Hz, 6H), 2.17 (t, J=7.5 Hz, 6H), 1.78-1.26 (m, 60H).

Production Example 13

Production of Compound 14 to be Presented Below

[Chemical Formula 17]

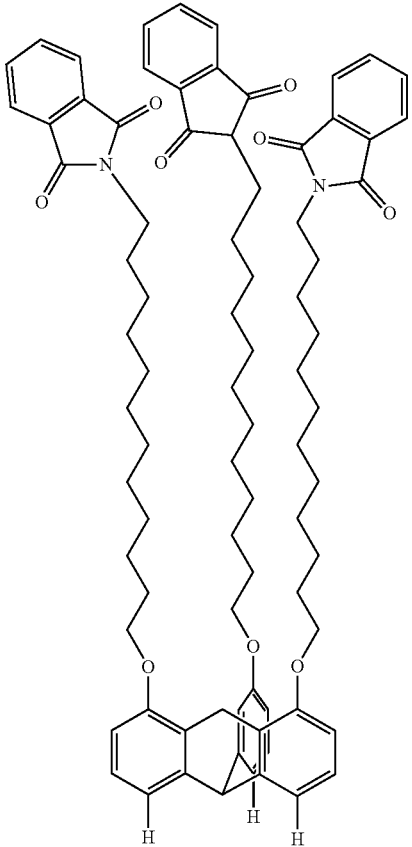

Compound 6 (245 mg, 0.810 mmol) produced in Production Example 3 was dissolved in 5.0 mL of dimethylformamide, and potassium carbonate (450 mg, 3.25 mmol) and N-(12-bromododecyl)phthalimide (1.15 g, 2.92 mmol) were added thereto, and the mixture was stirred for 8 hours at 70° C. To the reaction mixture, 100 mL of diethyl ether was added, the mixture was washed with water, and the organic layer was then dried over magnesium sulfate, filtered, and subjected to distillation under reduced pressure. The residue was subjected to silica gel column chromatography using a mixed solvent of hexane/chloroform (2/8, v/v) as a solvent, thereby obtaining Compound 14 (yield: 855 mg, 87%) of the title.

Compound 14:

$^1$H-NMR (400 MHz, CDCl$_3$): δ (ppm) 7.82 (m, 6H), 7.68 (m, 6H), 6.98 (d, J=7.2 Hz, 3H), 6.89 (s, 1H), 6.88 (t, J=8.1 Hz, 3H), 6.53 (d, J=8.1 Hz, 3H), 5.36 (s, 1H), 3.95 (t, J=6.4 Hz, 3H), 3.66 (t, J=7.3 Hz, 3H), 1.8-1.2 (m, 60H).

Production Example 14

Production of Compound 15 to be Presented Below

[Chemical Formula 18]

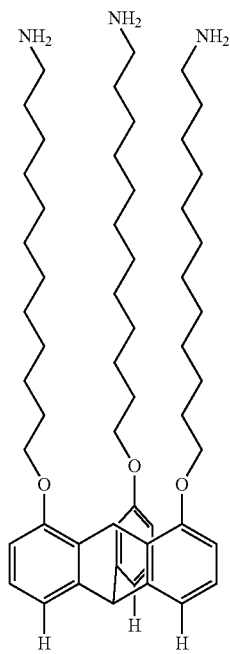

Compound 14 (187 mg, 0.153 mmol) produced in Production Example 13 was dissolved in 15.0 mL of tetrahydrofuran, hydrazine monohydrate (2.0 mL, 2.00 mmol) was added thereto, and the mixture was refluxed while heating for 12 hours. After the reaction mixture was cooled to room temperature, 150 mL of water was added thereto, and the precipitated solid was collected through filtration. After the precipitate thus filtered was washed with water, and the organic layer was dried over magnesium sulfate, filtered, and subjected to distillation under reduced pressure. The residue was dissolved in 2.0 mL of dimethylformamide to conduct the recrystallization thereof, thereby obtaining Compound 15 (yield: 100 mg, 76%) of the title.

Compound 15:

$^1$H-NMR (400 MHz, DMSO-$d_6$): δ (ppm) 7.05 (d, J=7.6 Hz, 3H), 6.91 (t, 7.6 Hz, 3H), 6.81 (s, 1H), 6.66 (d, J=7.6 Hz, 3H), 5.53 (s, 1H), 4.00 (t, J=6.4 Hz, 6H), 2.67 (t, J=7.5 Hz, 6H), 1.81 (m, 6H), 1.59 (m, 6H), 1.47-1.29 (m, 48H).

Production Example 15

Production of Compound 3 to be Presented Below

[Chemical Formula 19]

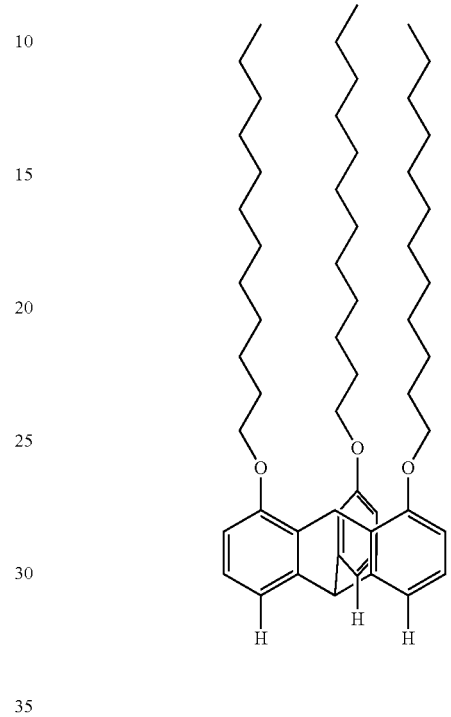

To Compound 6 (100 mg, 0.331 mmol) produced in Production Example 3 and potassium carbonate (274 mg, 1.98 mmol), 2.0 mL of dimethylformamide was added, the mixture was stirred, 1-bromododecane (990 mg, 3.97 mmol) was further added thereto, and the mixture was stirred for 8 hours at 75° C. while heating. The reaction mixture was cooled to room temperature, 300 mL of diethyl ether and water were added thereto, and the organic layer was separated. The organic layer was washed with brine and water, the organic layer was then dried over magnesium sulfate, and the solvent was then distilled off under reduced pressure. The residue was subjected to the size exclusion chromatography using chloroform as a solvent, thereby obtaining Compound 3 (yield: 213 mg, 89%) of the title as white powder.

Compound 3:

$^1$H-NMR (400 MHz, acetone-$d_6$): δ (ppm) 7.99 (d, J=7.2 Hz, 3H), 7.91 (s, 1H), 7.89 (t, J=7.6 Hz, 3H), 7.55 (d, J=8.1 Hz, 3H), 3.95 (t, J=6.4 Hz, 6H), 1.85 (q, J=7.1 Hz, 6H), 1.60-1.55 (m, 6H), 1.36-1.28 (m, 54H), 0.89 (t, J=6.8 Hz, 9H).

Production Example 16

Production of the Following Compound 16

[Chemical Formula 20]

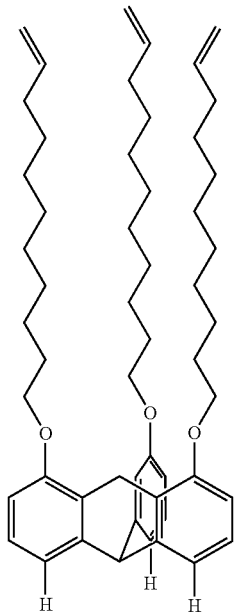

To Compound 6 (100 mg, 0.331 mmol) produced in Production Example 3 and potassium carbonate (365 mg, 2.64 mmol), 2.0 mL of dimethylformamide was added, the mixture was stirred, 11-bromododecane (608 mg, 2.61 mmol) was further added thereto, and the mixture was stirred for 12 hours at 80° C. while heating. The reaction mixture was cooled to room temperature, 200 mL of diethyl ether and water were added thereto, and the organic layer was separated. The organic layer was washed with water and brine, the organic layer was then dried over magnesium sulfate, and the solvent was then distilled off under reduced pressure. The residue was subjected to the size exclusion chromatography using chloroform as a solvent, thereby obtaining Compound 16 (yield: 187 mg, 75%) of the title as white powder.

Compound 16:

$^1$H-NMR (400 MHz, acetone-ds): δ (ppm) 6.99 (d, J=7.2 Hz, 3H), 6.89 (s, 1H), 6.87 (t, J=7.8 Hz, 3H), 6.54 (d, J=7.8 Hz, 3H), 5.37 (s, 1H), 3.96 (t, J=6.4 Hz, 6H), 2.19 (td, J=7.1 Hz, J=2.6 Hz, 6H), 1.94 (t, J=2.6 Hz, 3H), 1.85 (q, J=7.0 Hz, 6H), 1.58-1.50 (m, 12H), 1.41-1.35 (m, 24H).

Production Example 17

Production of the Following Compound 17

[Chemical Formula 21]

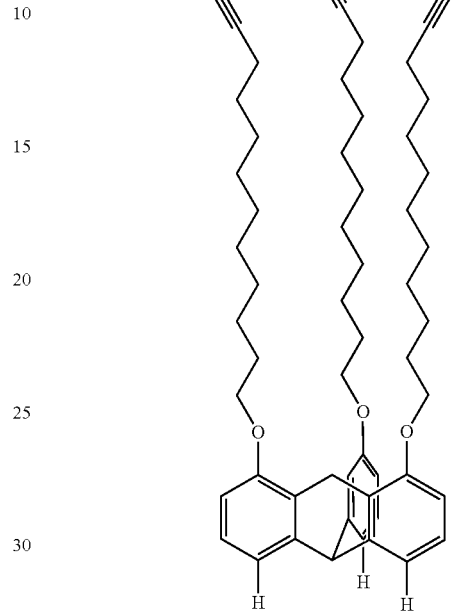

To Compound 6 (160 mg, 0.221 mmol) produced in Production Example 3 and potassium carbonate (365 mg, 2.64 mmol), 2.0 mL of dimethylformamide was added, the mixture was stirred, 11-bromododecyne (555 mg, 2.61 mmol) was further added thereto, and the mixture was stirred for 12 hours at 80° C. while heating. The reaction mixture was cooled to room temperature, 200 mL of diethyl ether and water were added thereto, and the organic layer was separated. The organic layer was washed with water and brine, the organic layer was then dried over magnesium sulfate, and the solvent was then distilled off under reduced pressure. The residue was subjected to the size exclusion chromatography using chloroform as a solvent, thereby obtaining Compound 17 (yield: 99.3 mg, 47%) of the title as white powder.

Compound 17:

$^1$H-NMR (300 MHz, acetone-d$_6$): δ (ppm) 7.00 (d, J=7.2 Hz, 3H), 6.90 (s, 1H), 6.87 (t, J=7.8 Hz, 3H), 6.55 (d, J=7.5 Hz, 3H), 5.87-5.75 (m, 3H), 5.04-4.92 (m, 6H), 5.37 (s, 1H), 3.96 (d, J=6.6 Hz, 6H), 2.08-2.01 (m, 6H), 1.85 (q, J=6.6 Hz, 6H), 1.65-1.51 (m, 12H), 1.36-1.32 (m, 24H).

Production Example 18

Production of the Following Compound 18

[Chemical Formula 22]

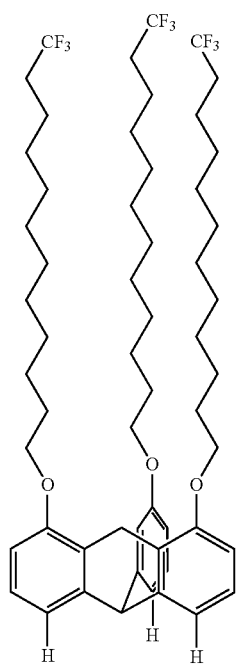

To Compound 16 (160 mg, 0.221 mmol) produced in Production Example 16, a trifluoromethylating agent (J. Am. Chem. Soc., 2011, 133, 16410) (316 mg, 1.00 mmol) represented by the following Formula:

[Chemical Formula 23]

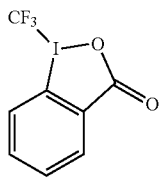

and copper(I) chloride (9.90 mg, 0.100 mmol), 2.0 mL of dimethyl formamide was added, and the mixture was frozen to degas and stirred for 30 minutes at 70° C. while heating under argon. To the reaction mixture, 300 mL of water was added, and the solid thus precipitated was separated by filtration and subjected to the silica gel chromatography using a mixed solvent of hexane-dichloromethane (2:1, v/v) as a developing solvent. To the white powder (119 mg) thus obtained, 5% palladium carbon (24 mg), 50 mL of tetrahydrofuran, and 50 mL of ethanol were added, and the mixture was stirred for 12 hours at room temperature under a hydrogen gas atmosphere. The reaction mixture was filtered through a pad of celite, and the solvent was distilled off under reduced pressure. The residue was subjected to the silica gel chromatography using a mixed solvent of hexane-dichloromethane (2:1, v/v) as a developing solvent, thereby obtaining Compound 18 (yield: 99.3 mg, 47%) of the title as white powder.

Compound 18:
$^1$H-NMR (400 MHz, CDCl$_3$): δ (ppm) 7.00 (d, 3H, J=7.4 Hz), 6.89 (s, 1H), 6.87 (dd, 3H, J=7.4, 7.4 Hz), 6.55 (d, 3H J=7.4 Hz), 5.37 (s, 1H), 3.96 (t, 6H, J=6.5 Hz), 1.85 (m, 6H), 1.61-1.51 (tt, 6H, J=6.5, 6.5 Hz), 1.43-1.29 (m, 36H).

Example 1

Production of Compound 4 According to the Following Reaction Formula

[Chemical Formula 24]

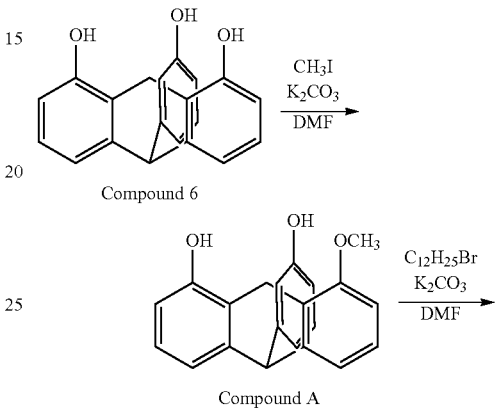

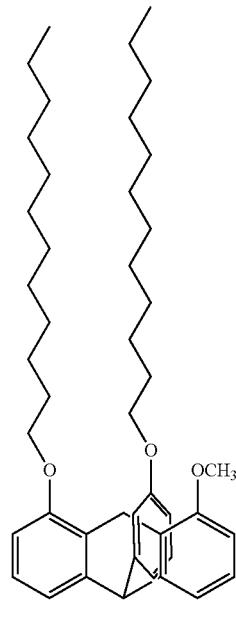

(1) Production of Compound A
(1,8-dihydroxy-13-methoxytriptycene)

Iodomethane (351 mg, 2.47 mmol) was mixed with a dimethylformamide (DMF) suspension (10.0 mL) of Compound 6 (500 mg, 1.65 mmol) produced in Production Example 3 and potassium carbonate (342 mg, 2.48 mmol), and the mixture was stirred for 12 hours at 75° C. The reaction mixture was cooled to room temperature, 500 mL of diethyl ether was added thereto, and the mixture was washed with 300 mL of water two times and with a saturated aqueous solution of sodium chloride one time. The organic layer was dried over magnesium sulfate and filtered, and the filtrate was then distilled off under reduced pressure. The residue was subjected to silica gel column chromatography using chloroform/acetone (7:3, v/v) as an eluent, thereby obtaining Compound A as a white solid in a yield of 48% (251 mg, 0.792 mmol).

Compound A:

IR (KBr, cm$^{-1}$): 3382, 3062, 3022, 2961, 2936, 2836, 1597, 1479, 1455, 1381, 1317, 1269, 1159, 1088, 1065, 1020, 974, 943, 861, 791, 755, 729, 594, 570, 469.

$^1$H-NMR (400 MHz, acetone-ds): δ (ppm) 8.30 (s, 2H), 7.05 (d, J=7.3 Hz, 1H), 6.95 (d, J=7.5 Hz, 2H), 6.94 (t, J=7.5 Hz, 1H), 6.88 (s, 1H), 6.77 (t, J=7.3 Hz, 2H), 6.66 (d, J=7.4 Hz, 1H), 6.55 (d, J=8.1 Hz, 2H), 5.48 (s, 1H), 3.83 (s, 3H).

APCI-TOF MS: calcd. for $C_{21}H_{16}O_3$[M]: m/z Calculated value: 316.11, Measured value: 316.11.

(2) Production of Compound 4
(1,8-bis(dodecoxy)-13-methoxytriptcene)

1-Bromododecane (1.18 g, 4.73 mmol) was mixed with a DMF suspension (5.0 mL) of Compound A (250 mg, 0.788 mmol) and potassium carbonate (653 mg, 4.73 mmol), and the mixture was stirred for 12 hours at 75° C. The reaction mixture was cooled to room temperature, 500 mL of diethyl ether was added thereto, and the mixture was washed with 300 mL of water two times and with a saturated aqueous solution of sodium chloride one time. The organic layer was dried over magnesium sulfate and filtered, and the filtrate was then distilled off under reduced pressure. The residue was subjected to silica gel column chromatography using chloroform as an eluent, thereby obtaining Compound 4 as a white solid in a yield of 82% (421 mg, 0.646 mmol).

Compound 4:

IR (KBr, cm$^{-1}$): 3855, 3435, 2922, 2853, 1598, 1485, 1467, 1439, 1396, 1324, 1283, 1198, 1104, 1065, 855, 787, 731, 642, 607, 593.

$^1$H-NMR (400 MHz, CDCl$_3$): δ (ppm) 7.00 (d, J=7.1 Hz, 1H), 6.99 (d, J=7.2 Hz, 2H), 6.89 (t, J=7.4 Hz, 1H), 6.89 (s, 1H), 6.87 (t, J=7.3 Hz, 2H), 6.57 (d, J=7.3 Hz, 1H), 6.56 (d, J=7.5 Hz, 2H), 5.37 (s, 1H), 4.02-3.92 (m, 4H). 3.84 (s, 3H), 1.91-1.79 (m, 4H), 1.65-1.50 (m, 4H), 1.44-1.24 (m, 35H), 0.89 (t, J=6.8 Hz, 6H).

APCI-TOF MS: calcd. for $C_{45}H_{64}O_3$[M]$^+$: m/z Calculated value: 652.49, Measured value: 652.49.

A disubstituted form of the compounds produced in Production Examples described above is also produced in the same manner in conformity to the method of Example 1 described above.

Example 2

Production of Film Using Compound 4 by Vapor Deposition Method

The substrate temperature of a silicon substrate was set to 25° C. and Compound 4 produced in Production Example 1 was heated to about 200° C. that was the melting point thereof or higher to conduct vacuum deposition using a usual vacuum deposition apparatus under a reduced pressure environment of 4×10$^{-4}$ Pa. The film thickness of the vapor deposited film thus obtained was 50 nm.

The molecular orientation in the film thus obtained was measured by the grazing incidence X-ray diffraction method (GIXD), and as a result, it has been revealed that the film is a regularly orientated molecular film having an interval of $d_{110}$ of 0.41 nm. In addition, the interval of $d_{001}$ is 2.11 nm.

It has been revealed that the interval of the triptycene skeletal structures in the orientated molecular film is 0.81 nm from this result as well.

The film formed on a silicon substrate by the method described above was annealed for 60 minutes at 120° C. The molecular orientation in the film thus obtained was measured by the grazing incidence X-ray diffraction method (GIXD), and as a result, a change has not been observed as the interval of $d_{110}$ is 0.41 nm. In addition, a significant change has not been observed as the interval of $d_{001}$ is 2.05 nm.

Example 3

Compound 4 produced in Example 1 was vacuum-deposited on a quartz substrate, a mica substrate, a polyimide substrate, and a PET substrate, respectively, by the same method as in Example 2. The thickness of the respective films thus obtained was 50 nm.

The molecular orientation in the respective films thus obtained was measured by GIXD in the same manner as in Example 2, and as a result, it has been revealed that the films are a regularly orientated molecular film having an interval of $d_{110}$ of about 0.41 nm.

Comparative Example 1

Production of Film Using Compound 3 by Vapor Deposition Method

The substrate temperature of a silicon substrate was set to 25° C. and Compound 3 produced in Production Example 15 was heated to about 200° C. that was the melting point thereof or higher to conduct vacuum deposition using a usual vacuum deposition apparatus under a reduced pressure environment of 4×10$^{-4}$ Pa. The film thickness of the vapor deposited film thus obtained was 50 nm.

The molecular orientation in the film thus obtained was measured by the grazing incidence X-ray diffraction method (GIXD), and as a result, it has been revealed that the film is a regularly orientated molecular film having an interval of $d_{110}$ of 0.41 nm. In addition, the interval of $d_{001}$ is 2.13 nm. It has been revealed that the interval of the triptycene skeletal structures in the orientated molecular film is 0.81 nm from this result as well.

The film formed on a silicon substrate by the method described above was annealed for 60 minutes at 120° C. The molecular orientation in the film thus obtained was measured by the grazing incidence X-ray diffraction method (GIXD), and as a result, a significant change has been observed as the interval of $d_{110}$ is 0.40 nm and the interval of $d_{001}$ is 2.30 nm.

Example 4

Production of DNTT (Dinaphthothienothiophene) Film Using Compound 4 Produced in Example 1

A toluene solution (200 μM, 50 μL) of Compound 4 was drop-casted on a Parylene (registered trademark, paraxylylene-based resin) film to form a film (5 nm) approximately consisting of a bilayer.

This was naturally dried, and DNTT (dinaphthothienothiophene) was formed thereon to have a thickness of about 30 nm by a vacuum deposition method. A photograph of the DNTT (dinaphthothienothiophene) film thus produced taken by an atomic force microscope (AFM) is illustrated in FIG. 6.

Comparative Example 2

A DNTT film was formed in the same manner as in Example 4 except that the film of Compound 4 was not formed.

A photograph thereof taken by an atomic force microscope (AFM) is illustrated in FIG. 4.

Comparative Example 3

A DNTT film was formed in the same manner as in Example 4 except that Compound 3 produced in Production Example 15 was used instead of the film using Compound 4.

A photograph thereof taken by an atomic force microscope (AFM) is illustrated in FIG. 5.

Example 5

An example of a high-performance transistor using Compound 4 in interface modification between a gate insulating film and an organic semiconductor film is described below.

The cross-sectional structure of the transistor manufactured is illustrated in FIG. 7. The transistor structure is a bottom gate top contact type. First, a gate electrode pattern composed of gold was formed on a polyimide film (product number: UPILEX 75S manufactured by UBE INDUSTRIES, LTD.) to be the substrate to have a thickness of 20 nm. A Parylene (registered trademark, paraxylylene-based resin) film having a thickness of 70 nm was formed thereon to obtain a gate insulating film. A solution of Compound 4 of the present invention was further drop-casted thereon and annealed for 1 hour at 120° C. to produce a multilayer molecular film having a thickness of 5 nm. DNTT (dinaphthothienothiophene) was patterned on this film composed of Compound 4 to have a thickness of 30 nm, and a gold electrode was attached thereon.

The electron field-effect mobility (mobility) of the transistor thus obtained was 1.5 cm²/Vs and the threshold voltage ($V_{TH}$) was −0.2 V.

Comparative Example 4

A transistor was manufactured in the same manner as in Example 5 except that the film of Compound 4 was not formed.

The electron field-effect mobility (mobility) of the transistor thus obtained was 0.8 cm²/Vs and the threshold voltage ($V_{TH}$) was −0.5 V.

Comparative Example 5

A transistor was manufactured in the same manner as in Example 5 except that Compound 3 produced in Production Example 15 was used instead of the film using Compound 4.

The electron field-effect mobility (mobility) of the transistor thus obtained was 1.2 cm²/Vs and the threshold voltage ($V_{TH}$) was −1.9 V.

FIG. 8 illustrates the measurement results of the DC bias stress resistance of the transistors of Example 5 and Comparative Example 5. In this measurement, a current change when a direct current voltage of −8 V was applied to between the drain and the source and −8 V to between the gate and the source was recorded.

FIG. 9 is a graph obtained by measuring the properties of the transistor of Example 5. In this measurement, a current change when a direct current voltage of −8 V was applied to between the drain and the source and from 0 V to −8 V to between the gate and the source was recorded. The vertical axis on the left side in FIG. 9 denotes the drain-source current ($I_{DS}$), the right vertical axis denotes the gate-source current ($I_{GS}$), and the horizontal axis denotes the gate-source voltage ($V_{GS}$).

The results have been obtained that all the important properties of a transistor are favorable, that is, the electron field-effect mobility of the transistor of Example 5 according to the present invention is higher, the threshold voltage thereof is lower, and the DC bias stress resistance thereof is higher when Example 5 is compared to Comparative Example 4 and Comparative Example 5.

INDUSTRIAL APPLICABILITY

The present invention can be formed into a film that exhibits extremely unique properties different from those of a self-assembled film of the conventional art and provides not only a thin film for an electronic device such as a thin film transistor but also a nanoscale thin film that has an extremely wide application range as a protective film, a film similar to a biological membrane, and the like. The present invention also provides a triptycene derivative useful as a novel film-forming material for forming the film, and an intermediate compound for producing the triptycene derivative.

Consequently, the present invention is useful in industrial fields using thin films such as thin film transistors, and has industrial applicability not only in the chemical industry but also in the electronic device industry and the like.

The invention claimed is:
1. A Janus-type triptycene derivative represented by the following Formula [I]:

[Chemical Formula 1]

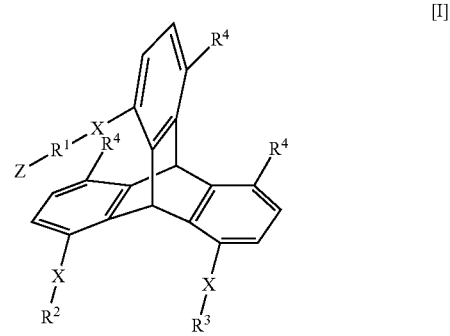

(in Formula [I], $R^1$ represents a divalent saturated or unsaturated hydrocarbon group having from 5 to 30 carbon atoms, wherein the hydrocarbon group may have at least one substituent, and at least one carbon atom in the hydrocarbon group may be substituted with an oxygen atom, a sulfur atom, a silicon atom, or —$NR^5$— (wherein $R^5$ represents a hydrogen atom, an alkyl group having from 1 to 10 carbon atoms, or an aryl group having from 6 to 30 carbon atoms);
$R^2$ represents a hydrogen atom or a saturated or unsaturated hydrocarbon group having from 1 to 4 carbon atoms;

R³ represents a group —R¹—Z, a hydrogen atom, or a saturated or unsaturated hydrocarbon group having from 1 to 4 carbon atoms;

R⁴ may be the same as or different from one another and each independently represents a hydrogen atom, a halogen atom, a hydroxyl group, a nitro group, a cyano group, an amino group, a monoalkyl-substituted amino group, a dialkyl-substituted amino group, an alkyl group which has from 1 to 10 carbon atoms and may have at least one substituent, an alkenyl group which has from 2 to 10 carbon atoms and may have at least one substituent, an alkynyl group which has from 2 to 10 carbon atoms and may have at least one substituent, an alkoxy group which has from 1 to 10 carbon and may have at least one substituent, an alkylthio group which has from 1 to 10 carbon atoms and may have at least one substituent, a formyl group, an alkylcarbonyl group which has from 1 to 10 carbon atoms and may have at least one substituent, an alkoxycarbonyl group which has from 1 to 10 carbon atoms and may have at least one substituent, an alkylcarbonyloxy group which has from 1 to 10 carbon atoms and may have at least one substituent, an aryl group which has from 6 to 30 carbon atoms and may have at least one substituent, or a 5- to 8-membered heteroaryl group which has from 1 to 5 hetero atoms selected from the group consisting of nitrogen atom, oxygen atom, and sulfur atom and has from 2 to 10 carbon atoms and may have at least one substituent;

X represents a linker group consisting of a divalent atomic group which has from 1 to 5 atoms selected from the group consisting of nitrogen atom, oxygen atom, sulfur atom, carbon atom, and silicon atom and may have at least one hydrogen atom; and Z represents a hydrogen atom, a group capable of binding to or adsorbing on a surface of a solid substrate; or an end group consisting of a monovalent atomic group which has from 1 to 15 atoms selected from the group consisting of nitrogen atom, oxygen atom, sulfur atom, carbon atom, phosphorus atom, halogen atom, and silicon atom and may have at least one hydrogen atom).

2. The Janus-type triptycene derivative according to claim 1, wherein X in Formula [I] is a divalent group represented by —CH₂—, —CH=CH—, —O—, or —NR⁶— (wherein R⁶ represents a hydrogen atom or an alkyl group having from 1 to 4 carbon atoms).

3. The Janus-type triptycene derivative according to claim 1, wherein R¹ in Formula [I] is an alkylene group having from 5 to 30 carbon atoms, an alkenylene group having from 5 to 30 carbon atoms, an alkynylene group having from 5 to 30 carbon atoms, or a divalent arylene group which contains at least one aryl ring having from 6 to 30 carbon atoms and in which total carbon atoms are from 6 to 60.

4. The Janus-type triptycene derivative according to claim 1, wherein Z in Formula [I] is a hydrogen atom, a haloalkyl group having from 1 to 10 carbon atoms, an alkenyl group having from 2 to 10 carbon atoms, an alkynyl group having from 2 to 10 carbon atoms, a hydroxyl group, —COOR⁷ (wherein R⁷ represents a hydrogen atom or an alkyl group which has from 1 to 5 carbon atoms and may have at least one substituent), —N(R⁸)₂ (wherein R⁸ may be the same as or different from each other and represents a hydrogen atom, an alkyl group which has from 1 to 5 carbon atoms and may have at least one substituent, or aryl group which has from 6 to 30 carbon atoms and may have at least one substituent), or —P(=O)(OR¹⁵)₂ (wherein each of R¹⁵ independently represents a hydrogen atom, an alkyl group having from 1 to 10 carbon atoms, or an aryl group having from 6 to 12 carbon atoms).

5. The Janus-type triptycene derivative according to claim 1, wherein R⁴ in Formula [I] is a hydrogen atom, a halogen atom, a hydroxyl group, a nitro group, an alkoxy group which has from 1 to 10 carbon atoms and may have at least one substituent, or an aryl group which has from 6 to 30 carbon atoms and may have at least one substituent.

6. The Janus-type triptycene derivative according to claim 1, wherein R² is an alkyl group having from 1 to 4 carbon atoms.

7. The Janus-type triptycene derivative according to claim 1, wherein R³ is a group —R¹—Z.

8. A film formed as the Janus-type triptycene derivatives according to claim 1 align in a self-assembled manner.

9. The film according to claim 8, wherein the Janus-type triptycene derivative has three benzene rings arranged in a three-blade shape as a skeletal structure and has three substituents on the same side of the skeletal structure, the benzene rings of the skeletal structures integrate in a nest shape, and the three substituents of the triptycene derivatives align in the same direction and integrate.

10. The film according to claim 8, wherein the film is a multilayer film.

11. The film according to claim 8, wherein the film is a monolayer.

12. A structure comprising the film according to claim 8 on a surface of a solid substrate.

13. The structure according to claim 12, wherein the structure constitutes a part of an electronic device.

14. The structure according to claim 13, wherein the electronic device is a thin film transistor (TFT).

15. An electronic device comprising a film formed as a Janus-type triptycene derivatives according to claim 8 align in a self-assembled manner.

16. The electronic device according to claim 15, wherein the electronic device is a transistor.

17. The electronic device according to claim 16, wherein the transistor is a thin film transistor.

18. A method for producing a film of Janus-type triptycene derivatives, the method comprising:
dissolving the Janus-type triptycene derivatives according to claim 1 in a solvent to obtain a solution;
coating the solution on a surface of a solid substrate or immersing a solid substrate in the solution; and
drying the solid substrate, thereby the film is formed on the solid substrate.

19. The method for producing the film according to claim 18, further comprising a step of annealing the film formed on the dried substrate.

20. The method for producing the film according to claim 18, wherein the solvent is a polar solvent.

21. The method for producing the film according to claim 18, wherein the Janus-type triptycene derivative has three benzene rings arranged in a three-blade shape as a skeletal structure and has three substituents on the same side of the skeletal structure, the benzene rings of the skeletal structures integrate in a nest shape, and the three substituents of the triptycene derivatives align in the same direction and integrate.

22. The method for producing the film according to claim 18, wherein the film is a multilayer film.

23. The method for producing the film according to claim 18, wherein the film is a monolayer.

24. A method for producing a structure having a film of Janus-type triptycene derivatives represented by Formula [I] formed on a surface of a solid substrate, the method comprising:
dissolving the Janus-type triptycene derivatives according to claim 1 in a solvent to obtain a solution;
coating the solution on the surface of the solid substrate or immersing the solid substrate in the solution; and
drying the solid substrate, thereby the film is formed on the solid substrate.

* * * * *